US010010364B2

(12) United States Patent
Harrington

(10) Patent No.: US 10,010,364 B2
(45) Date of Patent: Jul. 3, 2018

(54) DEVICES AND METHODS FOR DETECTION AND TREATMENT OF THE AORTICORENAL GANGLION

(71) Applicant: Douglas C. Harrington, Los Altos Hills, CA (US)

(72) Inventor: Douglas C. Harrington, Los Altos Hills, CA (US)

(73) Assignee: Halcyon Medical, Inc., Los Altos, CA (US)

( * ) Notice: Subject to any disclaimer, the term of this patent is extended or adjusted under 35 U.S.C. 154(b) by 92 days.

(21) Appl. No.: 14/269,001

(22) Filed: May 2, 2014

(65) Prior Publication Data

US 2014/0330267 A1    Nov. 6, 2014

Related U.S. Application Data

(60) Provisional application No. 61/818,749, filed on May 2, 2013, provisional application No. 61/905,770, filed on Nov. 18, 2013, provisional application No. 61/926,888, filed on Jan. 13, 2014.

(51) Int. Cl.
| | |
|---|---|
| *A61B 18/12* | (2006.01) |
| *A61B 18/14* | (2006.01) |
| *A61B 18/00* | (2006.01) |
| *A61N 1/05* | (2006.01) |

(Continued)

(52) U.S. Cl.
CPC ...... *A61B 18/1206* (2013.01); *A61B 18/1492* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/00839* (2013.01); *A61B 2018/1435* (2013.01); *A61B 2090/3735* (2016.02); *A61B 2090/3784* (2016.02); *A61N 1/0551* (2013.01); *A61N 1/36* (2013.01)

(58) Field of Classification Search
CPC ............ A61B 18/1206; A61B 18/1492; A61B 18/1435; A61B 2018/00267; A61B 2018/00434
See application file for complete search history.

(56) References Cited

U.S. PATENT DOCUMENTS

| | | | |
|---|---|---|---|
| 8,909,316 B2 * | 12/2014 | Ng | A61B 5/6853 600/381 |
| 2003/0216792 A1 | 11/2003 | Levin | |

(Continued)

FOREIGN PATENT DOCUMENTS

| | | |
|---|---|---|
| WO | WO 2010/067360 A2 | 6/2010 |
| WO | WO 2013/030743 A1 | 3/2013 |

OTHER PUBLICATIONS

WIPO, U.S. International Search Authority, International Search Report and Written Opinion dated Oct. 7, 2014 in International Patent Application No. PCT/US2014/036694, 9 pages.

*Primary Examiner* — Ronald Hupczey, Jr.
*Assistant Examiner* — Bo Ouyang
(74) *Attorney, Agent, or Firm* — Elliott, Ostrander & Preston, P.C.

(57) ABSTRACT

Devices and methods that regulate the innervation of the kidney by detection and modification of the aorticorenal ganglion. Devices for percutaneous detection and treatment of the aorticorenal ganglion via a blood vessel to modify renal sympathetic activity.

31 Claims, 15 Drawing Sheets

(51) Int. Cl.
*A61N 1/36* (2006.01)
*A61B 90/00* (2016.01)

(56) References Cited

U.S. PATENT DOCUMENTS

| | | | |
|---|---|---|---|
| 2007/0203549 A1* | 8/2007 | Demarais | A61N 1/05 607/72 |
| 2011/0200171 A1* | 8/2011 | Beetel | A61N 5/1042 378/65 |
| 2011/0257523 A1 | 10/2011 | Hastings et al. | |
| 2011/0307034 A1 | 12/2011 | Hastings | |
| 2012/0101413 A1* | 4/2012 | Beetel | A61B 18/082 601/3 |
| 2012/0136350 A1 | 5/2012 | Goshgarian et al. | |
| 2012/0265198 A1* | 10/2012 | Crow | A61B 18/1492 606/41 |
| 2012/0265227 A1* | 10/2012 | Sverdlik | A61B 17/22012 606/169 |
| 2012/0290024 A1 | 11/2012 | Zhang et al. | |

\* cited by examiner

DEVICES AND METHODS FOR DETECTION AND TREATMENT OF THE AORTICORENAL GANGLION

RELATED APPLICATIONS

This application claims priority to U.S. Provisional Application Ser. No. 61/818,749 filed May 2, 2013 entitled Device And Methods For Aorticorenal Ganglion Treatment, U.S. Provisional Application Ser. No. 61/905,770 filed Nov. 18, 2013 entitled Devices And Methods For Detection And Treatment Of The Aorticorenal Ganglion, and U.S. Provisional Application Ser. No. 61/926,888 filed Jan. 13, 2014 entitled Devices And Methods For Detection And Treatment Of The Aorticorenal Ganglion, all of which are hereby incorporated herein by reference in their entireties.

BACKGROUND OF THE INVENTION

Hypertension or abnormally high blood pressure is a growing public health concern for which successful treatment often remains elusive. Sixty-seven million Americans—about one-third of the adult population—have high blood pressure and these numbers are increasing as the population ages and obesity accelerates.

Hypertension is more common in men than women and afflicts approximately 50% of the population over the age of 65. Hypertension is serious because people with the condition have a higher risk for heart disease and other medical problems than people with normal blood pressure. If left untreated, hypertension can lead to arteriosclerosis, heart attack, stroke, enlarged heart and kidney damage.

Blood pressure is highest when the heart beats to push blood out into the arteries. When the heart relaxes to fill with blood again, the pressure is at its lowest point. Blood pressure when the heart beats is called systolic pressure. Blood pressure when the heart is at rest is called diastolic pressure. When blood pressure is measured, the systolic pressure is stated first and the diastolic pressure second. Blood pressure is measured in millimeters of mercury (mm Hg). For example, if a person's systolic pressure is 120 and diastolic pressure is 80, it is written as 120/80 mm Hg. Blood pressure lower than 120/80 mm Hg is considered normal.

A significant percentage of patients with uncontrolled hypertension fail to meet therapeutic targets despite taking multiple drug therapies at the highest tolerated doses, a phenomenon called resistant hypertension. This suggests there is an underlying pathophysiology resistant to current pharmacological approaches. Innovative therapeutic approaches are particularly relevant for these patients, as their condition puts them at high risk of major cardiovascular events.

The sympathetic nerve innervation of the kidney is implicated in the pathogenesis of hypertension through effects on rennin secretion, increased plasma rennin activity that leads to sodium and water retention, and reduction of renal (kidney) blood flow. As a result, a succession of therapeutic approaches has targeted the sympathetic nervous system to modulate hypertension, with varying success.

The sympathetic nerve innervation of the kidney is achieved through a dense network of postganglionic axons (nerves or nerve fibers) that innervate the kidney. This network of nerve fibers is often referred to as the renal plexus and runs alongside the renal artery and enters the hilum of the kidney. Thereafter, they divide into smaller nerve bundles following the blood vessels and penetrate cortical and juxtamedullary areas.

Preganglionic neuronal cell bodies are located in the intermediolateral cell column of the spinal cord. Preganglionic axons pass through the paravertebral ganglia (do not synapse) to become the lesser thoracic splanchnic nerve and least thoracic splanchnic nerve and travel to the aorticorenal ganglion which is located at the origin of the renal artery from the abdominal aorta. Postganglionic axons then enter the renal plexus, where they play an important role in the regulation of blood pressure by effecting renin release. The renal plexus contains only sympathetic components. There is no (or at least very minimal) parasympathetic innervation of the kidney.

As a result of the renal sympathetic nerves being implicated in the pathophysiology of systemic hypertension, a succession of therapeutic approaches has targeted the sympathetic nervous system to modulate hypertension, with varying success.

Surgical sympathectomy, the surgical cutting of a sympathetic nerve, was attempted more than 40 years ago in patients with malignant hypertension. Malignant hypertension was a devastating disease with a five-year mortality rate of almost 100%, thus interventional approaches have been tested for its treatment given the lack of effective drug therapy at the time. Sympathectomy was mainly applied in patients with severe or malignant hypertension, as well as patients with cardiovascular deterioration despite relatively good blood pressure reduction by other means.

Sympathectomy, also termed splanchnicectomy, was performed either in one or two stages, required a prolonged hospital stay (2-4 weeks) and a long recovery period (1-2 months) and importantly had to be performed by a highly skilled surgeon. It was thus performed only in a few select centers in the U.S. and Europe.

Sympathectomy proved to be effective in reducing blood pressure immediately postoperatively, and the results were maintained in the long term in most patients. Survival rates were also demonstrated to be high for patients undergoing the procedure. The two major limitations of splanchnicectomy were the required surgical expertise and the frequent adverse events occurring with this procedure. Adverse events were common and included orthostatic hypotension (very low blood pressure when standing up), orthostatic tachycardia, palpitations, breathlessness, anhidrosis (lack of sweating), cold hands, intestinal disturbances, sexual dysfunction, thoracic duct injuries and atelectasis (collapse of the lung).

After the introduction of antihypertensive drugs and due to its poor patient tolerance and surgical difficulty, sympathectomy was reserved for patients who failed to respond to antihypertensive therapy or could not tolerate it.

Recent studies have focused on using thermal energy delivered through a percutaneous approach to achieve renal nerve denervation. Renal denervation performed this way is designed to damage the renal nerve fibers along the length of the artery using thermal energy to block renal nerve activity, thus neutralize the effect of the renal sympathetic system which is involved in the development of hypertension. Percutaneous thermal device based renal nerve denervation may achieve such objectives, but is limited to appropriate renovascular anatomy. For example, patients diagnosed with renal arteriogram are excluded from treatment with the Simplicity™ Renal Denervation System (Medtronic, Minneapolis, Minn.) if renal artery diameter is less than 4 mm or renal artery length is less than 20 mm. Patients with accessory renal arteries, approximately 20-30% of the patient population, are also excluded from treatment.

Renal nerve denervation has also raised concerns of complications arising from significant amount of thermal endothelial damage required to create a complete renal nerve block along the length of the renal artery. Cases of renal artery stenosis after thermal renal nerve denervation have been reported in the literature.

As described above, the aorticorenal ganglion plays an import role in renal function including blood pressure regulation. Maillet (Innervation sympathique du rein: son role trophique. Acta Neuroveg., Part II, 20:337-371, 1960) describes various lesions of the renal parenchyma (functional tissue of the kidney, including the nephrons) after the chemical destruction of the aorticorenal ganglion in an animal model. Carbolic acid (5%) was brushed on the left aorticorenal ganglion or the left renal plexus. The renal parenchyma changes between the two techniques were shown to be identical.

Dolezel (Monoaminergic innervation of the kidney. Aorticorenal ganglion—a sympathetic, monoaminergic ganglion supplying the renal vessels. Experientia, 23:109-111, 1967) extirpated the left aorticorenal ganglion from 8 canines. 6-8 days later the left kidney was harvested and examined. Throughout the whole kidney the monoaminergic nerves terminating on the surface of the media of arteries, on the vasa recta, on the veins, in the fibrous skeleton of the kidney, and in the muscular part of the pelvic wall showed complete degeneration.

Norvell (Aorticorenal ganglion and its role in renal innervation. J. Comp. Neurol., 133:101-111, 1968) describes removing the aorticorenal ganglia from one side of 14 adult felines. Two weeks later, the kidneys were harvested and examined. Norvell observed that the large bundle of nerve fibers which are normally present in the perivascular connective tissue of the control kidney were found less frequently in the experimental kidneys. In the control kidneys, at least one, and sometimes several bundles of nerve fibers, was associated with any large blood vessel observed under the microscope. This was not the case in the experimental kidneys. It was difficult to find even a small bundle of nerve fibers in the area around the blood vessels. Fine nerve fibers going to the tubules were even more difficult to locate. Norvell concluded from the reduction of nerve fibers seen in the cat after removal of the aorticorenal ganglion, that this ganglion is important in both tubular and vascular innervation.

Various animal studies have shown that electrically stimulating renal nerves influences changes in renal hemodynamics such as renal blood flow (RBF) and glomerular filtration rate (GFR). From these animal studies emerged the concept of the graded response of the renal neuroeffectors to graded increase in the frequency of renal sympathetic nerve stimulation. At the lower frequency range ($\approx 0.5$ Hz), there is stimulation of renin secretion rate (RSR), without effects on urinary sodium excretion ($U_{NA}V$), RBF or GFR. At slightly higher frequencies ($\approx 1.0$ Hz), there is both stimulation of RSR and a decrease in $U_{NA}V$, without effects on RBF or GFR. At higher frequencies ($\approx 2.0$ Hz), there is stimulation of RSR and a decrease in $U_{NA}V$ and renal vasoconstriction, with decrease RBF (Gerald F. DiBona, Neural Control of the Kidney Past, Present and Future, Hypertension 2003; 41 [part 2]:621-624)

There is the need for a method and device that can regulate the innervation of the kidney to control diseases related to kidney function including hypertension without the limitations associated with only targeting renal nerve fibers with thermal energy.

SUMMARY OF THE INVENTION

The invention relates to devices and methods for treating hypertension and its related conditions. The method includes percutaneous modification of the aorticorenal ganglion and/or postganglionic renal nerves which results in a decrease or cessation of kidney nerve activity involved in the development of hypertension. The method can include but is not limited to the use of thermal, cryogenic, electrical, chemical, radiation, pharmacological and mechanical techniques to modify or neutralize the ganglion by means of a catheter.

Embodiments of the present invention are directed to a catheter assembly including a tissue modifying element or elements located approximately at the distal end of said catheter. One method involves percutaneous placement of the catheter in the renal artery in proximity to the aorticorenal ganglion followed by activation of the tissue modifying element. Activation modifies (e.g. ablates when radiofrequency energy is employed) the ganglion, creating disruption of nerve signals leading to the kidney. Other methods involve percutaneous placement of the catheter in any of the other body lumens in proximity to the aorticorenal ganglion including but not limited to abdominal aorta, vena cava, renal vein and ostia.

In accordance with an aspect of the current invention, an aorticorenal ganglion modifying catheter comprises an elongated catheter body extending longitudinally between a proximal end and a distal end along a longitudinal axis and a tissue modifying element or elements attached to the catheter body, elements to be utilized by activation which results in ganglionic tissue modification. One embodiment of the present invention is directed to a catheter assembly including a single monopolar radiofrequency electrode element located at the distal end of said catheter. In this embodiment the proximal end of the catheter is connected to an electrosurgical generator which in turn is connected to a dispersive electrode pad attached to the patient's skin creating a closed electrical circuit when electrode element is in tissue contact. When activated, radiofrequency energy travels through tissue adjacent to electrode and heats tissue resulting in tissue ablation and modification of the aorticorenal ganglion.

Another embodiment of the present invention is directed to a catheter assembly including a multi-electrode bipolar radiofrequency electrode element located at the distal end of said catheter. Use is similar to monopolar catheter but does not require the use of dispersive electrode pad. Another embodiment of the present invention is directed to radiofrequency electrode element with a cooling feature at the distal end of said catheter. Cooling the RF electrode element during activation has several benefits including limiting endothelial tissue damage to the vessel wall and creating deeper tissue modification (e.g. deeper lesions) if desired. Cooling the RF electrode element allows for higher temperatures thus deeper lesions by preventing high impedance electrosurgical generator shut down which occurs when blood coagulation collects on the higher temperature electrode elements. Cooling mechanism may incorporate a peltier effect device, cooled fluid or gas circulated in catheter distal tip. One example of cooling the electrode element involves flushing saline through catheter body and out of through-holes manufactured into the electrode element into the blood stream during radiofrequency energy activation, thus cooling the hotter electrode element with the cooler fluid through heat transfer.

In accordance with an aspect of the current invention, an aorticorenal ganglion modifying catheter comprises an elongated catheter body extending longitudinally between a proximal end and a distal end along a longitudinal axis and a balloon element assembly connected to the catheter body comprising radiofrequency electrode element attached to outer surface of balloon element. Balloon element has a proximal end connected to catheter body and a distal end. Balloon element is movable between a collapsed configuration and an expanded configuration. When balloon element is in proximity of aorticorenal ganglion, balloon element is expanded allowing for tissue contact with radiofrequency electrode element. Ganglionic tissue modification is achieved as previously described with monopolar and bipolar electrode element catheters.

In accordance with an aspect of the current invention, an aorticorenal ganglion modifying catheter comprises an elongated catheter body extending longitudinally between a proximal end and a distal end along a longitudinal axis and a basket element assembly connected to the catheter body comprising radiofrequency electrode elements attached to outer surface of basket element. Basket element has a proximal end connected to catheter body and a distal end. Basket element is movable between a collapsed configuration and an expanded configuration. When basket element is in proximity of aorticorenal ganglion, basket element is expanded allowing for tissue contact with radiofrequency electrode element. Ganglionic tissue modification is achieved as previously described with monopolar and bipolar electrode element catheters.

In accordance with an aspect of the current invention, an aorticorenal ganglion modifying catheter comprises an elongated catheter body extending longitudinally between a proximal end and a distal end along a longitudinal axis and a coil element assembly connected to the catheter body comprising radiofrequency electrode elements attached to surface of coil element. Coil element has a proximal end connected to catheter body and a distal end. Coil element is movable between a collapsed configuration and an expanded configuration. When coil element is in proximity of aorticorenal ganglion, coil element is expanded allowing for tissue contact with radiofrequency electrode element. Ganglionic tissue modification is achieved as previously described with monopolar and bipolar electrode element catheters.

In accordance with an aspect of the current invention, an aorticorenal ganglion modifying catheter comprises an elongated catheter body extending longitudinally between a proximal end and a distal end along a longitudinal axis and a radiofrequency electrode needle element contained within the catheter body. Radiofrequency electrode element can comprise either a monopolar or bipolar design and is movable between a retracted arrangement and a slidably advanced arrangement. One method involves percutaneous placement of the catheter in proximity to the aorticorenal ganglion, advancement of the radiofrequency electrode needle element through the vessel wall in juxtaposition to or within ganglion followed by activation of the tissue modifying electrode needle. Ganglionic tissue modification is achieved as previously described with monopolar and bipolar electrode element catheters.

Anatomically, the aorticorenal ganglion may be located just superior, anterior or inferior to the renal artery. One method of treatment involves creating tissue modification (e.g. tissue ablation when radiofrequency energy is employed) in the anatomic regions associated with the location of the aorticorenal ganglion. The shape of such a lesion would generally resemble a half toroid or half doughnut or horseshoe shaped tissue modification zone. Lesion shape can be contiguous or contain discrete segments that generally look similar to a half toroid in shape.

Half toroid shaped lesions can be created with previously disclosed embodiments of the current invention or with various design modifications of the previously disclosed embodiments. One method involves percutaneous placement and treatment with the monopolar radiofrequency aorticorenal ganglion modifying catheter in discrete segments along the vessel. For example, radiofrequency electrode element can be repositioned for tissue contact and activated in a superior, anterior and inferior position with the renal artery adjacent the ostium. Shape of tissue modification (e.g. lesion) will generally look similar to a half toroid.

Aorticorenal ganglion modifying catheters comprising either a balloon element, basket element or coil element previously disclosed can also be modified to create a half toroid shape lesions by bias positioning of the radiofrequency electrode elements. For example, electrode elements may be positioned on superior, anterior and inferior surface of balloon, basket or coil. One method involves placement of modified balloon, basket or coil catheter within renal artery so that tissue contact with electrode elements is superior, anterior and inferior to renal artery when balloon, basket or coil are expanded, followed by activation of the tissue modifying electrodes as previously described.

Aorticorenal ganglion modifying catheter comprising a radiofrequency electrode needle element previously disclosed can also be modified to create a half toroid shape lesion by biased positioning of more than one electrode needle element. For example, two or more electrode needle elements may be attached to the superior, anterior and inferior catheter body. One method involves placement of modified multi-needle element catheter within renal artery so that advancement of radiofrequency electrode needle elements through vessel wall is superior, anterior and inferior to renal artery, followed by activation of the tissue modifying needle electrodes as previously described.

In animal models, the aorticorenal ganglion has been located between the renal artery and renal vein. One method of treatment involves percutaneous placement of aorticorenal ganglion modifying catheter into the renal vein for modification of the aorticorenal ganglion.

Present invention also relates to devices and methods for detection of the aorticorenal ganglion by stimulating the aorticorenal ganglion and measuring resulting physiological responses. Examples of electrically stimulated physiological responses detectable at approximately 2 to 20 Hz stimulation include renal vasoconstriction, decreased RBF, decreased GFR and kidney and renal vasculature pulsations. Electrical stimulation can also be applied at approximately 50 Hz to stimulate sensory (afferent) nerves resulting in patient sensation and feedback to the medical staff. Detection method using electrical stimulation includes percutaneous placement of a tissue stimulating radiofrequency catheter with distal tip electrode in the renal vasculature adjacent to the aorticorenal ganglion followed by delivery of electrical energy (e.g. 15 volts, 5 Hz, 0.500 msec. pulse duration) through said tip into vessel wall. Stimulation of the ganglion will cause a detectable physiological response such as renal vasoconstriction, decreased RBF, reduced GFR and pulsations of the kidney and renal vasculature.

Renal vasoconstriction caused by electrical stimulation of the ganglion may be evaluated by measuring the change in renal artery diameter with diagnostic technologies such as Magnetic Resonance Angiogram (MRA), Angiography, Sonography (ultrasound), intravascular ultrasound (IVUS) (e.g. Eagle Eye® Platinum Catheter, Volcano Corporation, San Diego Calif.), and Optical Coherence Tomography (OCT) (e.g. Dragonfly™ Duo OCT Imaging Catheter, St. Jude Medical, St. Paul, Minn.). Vasoconstriction may also be evaluated with tissue stimulating catheter embodying a balloon, basket, coil or the like element by measuring the change in radial dimensions of the element during stimulation. For example, balloon element with radiopaque markers attached to the surface of a compliant balloon and placed within renal vessel will radially converge, as observed under fluoroscopy, during ganglia or nerve stimulation. Element may also transmit compression data (in the form of pressure increase for balloon element with pressure transducer embodiment) to an external source for vasoconstriction assessment.

Change in renal blood flow caused by electrical stimulation of the ganglion may be evaluated directly and/or indirectly with diagnostic technologies such as external Doppler Sonography and Intravascular Doppler Sonography which measures blood flow velocity (e.g. FloWire® Doppler Guide Wire, Volcano Corporation, San Diego Calif.) and Thermal Dilution Catheter which measures blood flow (e.g. Swan-Ganz catheter, Edwards Life Science, Irvine Calif.).

Kidney and renal artery pulsations caused by electrical stimulation of the ganglion may be visualized and evaluated with diagnostic technologies such as Magnetic Resonance Angiography (MRA), Angiography, Sonography and Doppler Sonography.

Kidney and renal artery pulsations caused by electrical stimulation of the ganglion which creates blood pressure pulsations in the renal artery may be evaluated with diagnostic technologies such as Intravascular Pressure Wire which measures blood pressure (e.g. Verrata™ Pressure Guide Wire, Volcano Corporation, San Diego Calif.).

Tissue stimulating device and/or physiological measurement device (diagnostic technologies) can be incorporated as elements into aorticorenal ganglion modifying catheter. Tissue stimulating element may also be used as tissue modifying element, for example when metallic electrodes are used for electrical stimulation and radiofrequency ablation. Tissue stimulating element may incorporate one or multiple distal tip electrodes and can be designed as a basket electrode, coil electrode, balloon electrode or the like and as previously disclosed in embodiments of the aorticorenal ganglion modifying catheter.

Procedure steps for detection, modification and treatment verification of aorticorenal ganglion or other targeted nerve tissue may be as follows: Step 1, locate aorticorenal ganglion by applying stimulation and analyzing a physiological response. Step 2, modification of aorticorenal ganglion (e.g. tissue ablation with RF energy). Step 3 (optional), confirmation of adequate modification of aorticorenal ganglion by reapplying stimulation and analyzing the physiological response.

Embodiments of the present invention are directed to a catheter assembly including a tissue stimulating element and a tissue modifying element located approximately at the distal end of said catheter. Stimulating element and tissue modifying element may be integral or separate components. One method of detection and modification of the aorticorenal ganglion involves percutaneous placement of said catheter in the renal artery with stimulating element and modifying element adjacent the vessel wall followed by electrical stimulation of adjacent tissue with stimulating element. Ganglion location is determined with a measurable or observable physiological response (e.g. renal vasoconstriction as detected during fluoroscopy). Modification of the ganglion then proceeds (e.g. ablation when radiofrequency energy is employed) by activation of the tissue modifying element adjacent stimulated tissue, resulting in disruption of the nerve signals leading to the kidney. Sufficient ganglion treatment may be confirmed by reapplying electrical stimulation to modified tissue and discerning differences to the pre-treatment physiological response. Method of detection and modification with said catheter may also be performed in other vessels including the renal vein, vena cava or aorta.

Embodiments of the present invention are also directed to a catheter assembly including a tissue modifying element and a physiological measurement element located approximately at the distal end of said catheter. One method of modification of the aorticorenal ganglion involves percutaneous placement of said catheter in the renal artery followed by baseline physiological measurements with physiological measurement element. Modification of the ganglion then proceeds by activation of the tissue modifying element, resulting in disruption of the nerve signals leading to the kidney. Acceptable nerve signal disruption may be confirmed by comparing the differences between pre-tissue modification physiological responses to post-tissue modification physiological responses with said catheter. Modification of the ganglion and physiological response measurements may be performed separately or simultaneously, with the latter allowing for a cessation of tissue modification once acceptable nerve disruption as measured by a physiological response is achieved.

Another embodiment of the present invention is directed to a catheter assembly including a tissue stimulating element, physiological measurement element and tissue modifying element located approximately at the distal end of said catheter. Tissue stimulating element, physiological measurement element and tissue modifying element may be integral or separate components of said catheter. One method of detection and modification of the aorticorenal ganglion involves percutaneous placement of the catheter in the renal artery with stimulating element and tissue modifying element adjacent the vessel wall and physiological measurement element proximate aforementioned elements. Electrical stimulation is applied with tissue stimulating element to adjacent tissue followed by measurement of a response to the stimuli with the physiological measurement element. Ganglia detection is confirmed when pre-established physiological response measurements for targeted ganglion are achieved. Modification of the ganglion then proceeds (e.g. ablation when radiofrequency energy is employed) by activation of the tissue modifying element adjacent stimulated tissue, resulting in disruption of the nerve signals leading to the kidney. Adequate ganglion treatment may be confirmed by reapplying electrical stimulation to modified tissue and comparing differences to the pre-treatment physiological response. Method of detection and modification of ganglia and nerve tissue with said catheter may also be performed within other vessels including the renal vein, vena cava or aorta. Present invention may also target and treat alternative ganglia, splanchnic nerves and the renal plexus.

Embodiments of the present invention are also directed to a two catheter arrangement embodying a tissue stimulating element, tissue modifying element and physiological measurement element. One arrangement including a first catheter with a tissue stimulating element and tissue modifying element at the distal end of said first catheter and a second catheter with a physiological measurement element at the distal end of said second catheter. An alternative arrangement including a first catheter with a tissue stimulating element and physiological measurement element at the distal end of said first catheter and second catheter with a tissue modifying element at the distal end of said second catheter. An alternative arrangement including a first catheter with a tissue modifying element and physiological measurement element at the distal end of said first catheter and second catheter with a tissue stimulating element at the distal end of said second catheter. One method of detection and modification of the aorticorenal ganglion with said two catheter arrangement involves percutaneous placement of first catheter with tissue stimulating element and tissue modifying element in the renal vein and percutaneous placement of second catheter with physiological measurement element in the renal artery. Electrical stimulation of adjacent tissue is applied with said first catheter and physiological response is ascertained with said second catheter to locate the ganglion as described previously. Modification of the ganglion then proceeds by activation of the tissue modifying element on said first catheter followed by verification of treatment by reapplying stimulation to modified tissue with said first catheter and analyzing physiological responses with said second catheter. Methods of treatment with two catheter arrangements may also be performed in various combinations of placement of devices in the renal vein, renal artery, vena cava and aorta. For example, placement of first catheter with a tissue stimulating element and tissue modifying element placed in the vena cava and second catheter with physiological measurement element placed in the renal artery.

Embodiments of the present invention are also directed to a two catheter arrangement embodying a tissue stimulating element and tissue modifying element. One said arrangement including a first catheter with a tissue stimulating element at the distal end of said first catheter and second catheter with a tissue modifying element at the distal end of said second catheter. One method of detection and modification of the aorticorenal ganglion with said two catheter arrangement involves percutaneous placement of the first catheter in the renal vein with stimulating element and percutaneous placement of second catheter with tissue modifying element in the aforementioned renal vein. First catheter delivers electrical stimulation to adjacent tissue followed by measurement of a physiological response (e.g. renal vasoconstriction as detected during fluoroscopy) to locate the ganglion. Modification of the ganglion then proceeds with second catheter by activation of the tissue modifying element adjacent tissue (e.g. ablation when high intensity focused ultrasound is employed), resulting in disruption of the nerve signals leading to the kidney. Sufficient ganglion treatment may be confirmed by reapplying electrical stimulation to modified tissue and analyzing differences to the pre-treatment physiological response. Method of nerve detection and tissue modification with said two catheter arrangement may also be performed in various combinations within the renal veins, arteries, vena cava and aorta.

Embodiments of the present invention are also directed to a three catheter arrangement. One said arrangement including a first catheter with a tissue stimulating element at the distal end of said first catheter, second catheter with a physiological measurement element at the distal end of said second catheter and third catheter with a tissue modifying element at the distal end of said third catheter. Method of detection and modification of ganglia with three catheter arrangement is similar to the previously described procedures with percutaneous placement of said catheters in the renal veins, arteries, vena cava and aorta. For example, one method involves percutaneous placement of the first catheter with tissue stimulating element in the aorta, second catheter with physiological measurement element in the renal artery and third catheter with tissue modifying element in the renal vein. Electrical stimulation is applied to the adjacent tissue in the aorta with first catheter, stimulating the splanchnic nerve followed by measurement of a physiological response in the renal artery with second catheter. Renal innervation of the stimulated nerve is confirmed when physiological response (e.g. renal artery diameter contraction) is detected with said second catheter. Modification of the nerve tissue then proceeds by activation of the tissue modifying element with said third catheter. Verification of nerve treatment may be confirmed by reapplying electrical stimulation with said first catheter and analyzing physiological response changes with said second catheter.

Percutaneous placement of the catheter assembly may be accomplished using any of the currently available techniques and ancillary equipment for abdominal aorta and renal artery interventions including guided sheaths, steerable distal tip assemblies and over the wire configurations employed for diagnostic and therapeutic devices. There may be other means to modify the aorticorenal ganglion not specifically described in one of the inventions embodiments, but it is to be understood that the description is not meant as a limitation since further modifications may suggest themselves or be apparent to those skilled in the art.

The invention disclosed herein may be utilized for treatment of other clinical conditions influenced by kidney nerve activity including kidney disease, congestive heart failure, obstructive sleep apnea, diabetes and others. The invention disclosed herein may be utilized for modification of other tissues including splanchnic nerves, renal nerves and ganglia apart from aorticorenal ganglia.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF THE INVENTION

Figure 1:
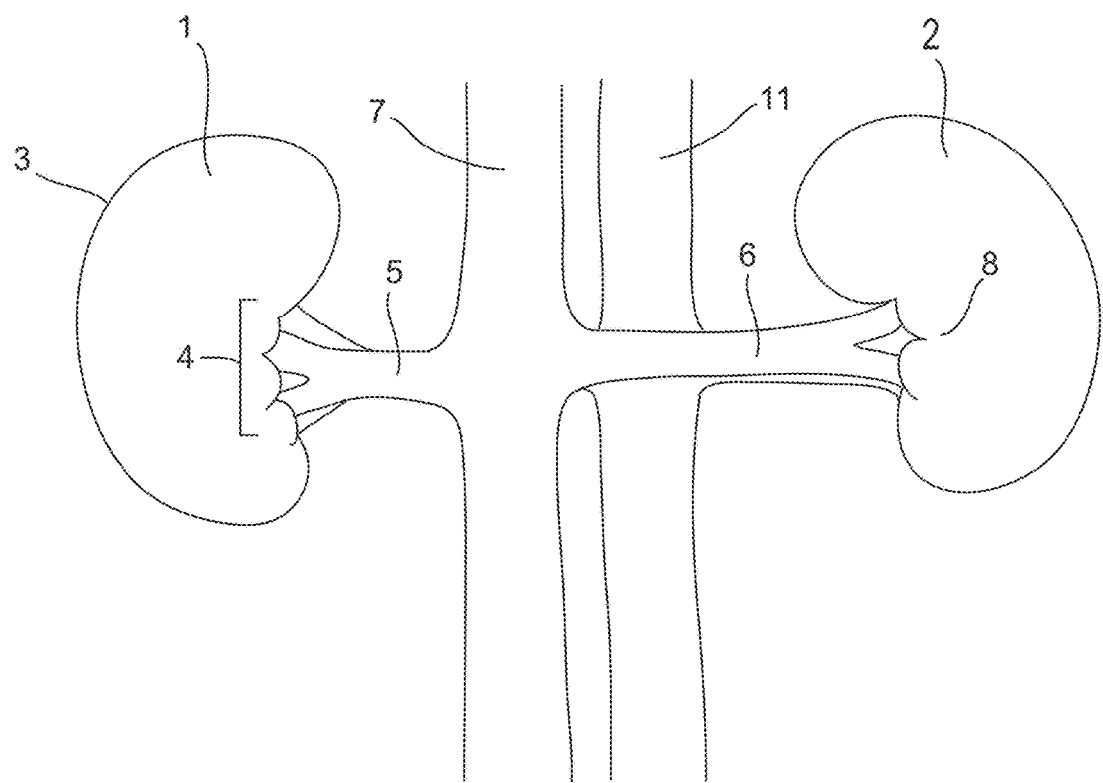
FIG. 1 is an anterior view of human kidneys and supporting vasculature.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 2:
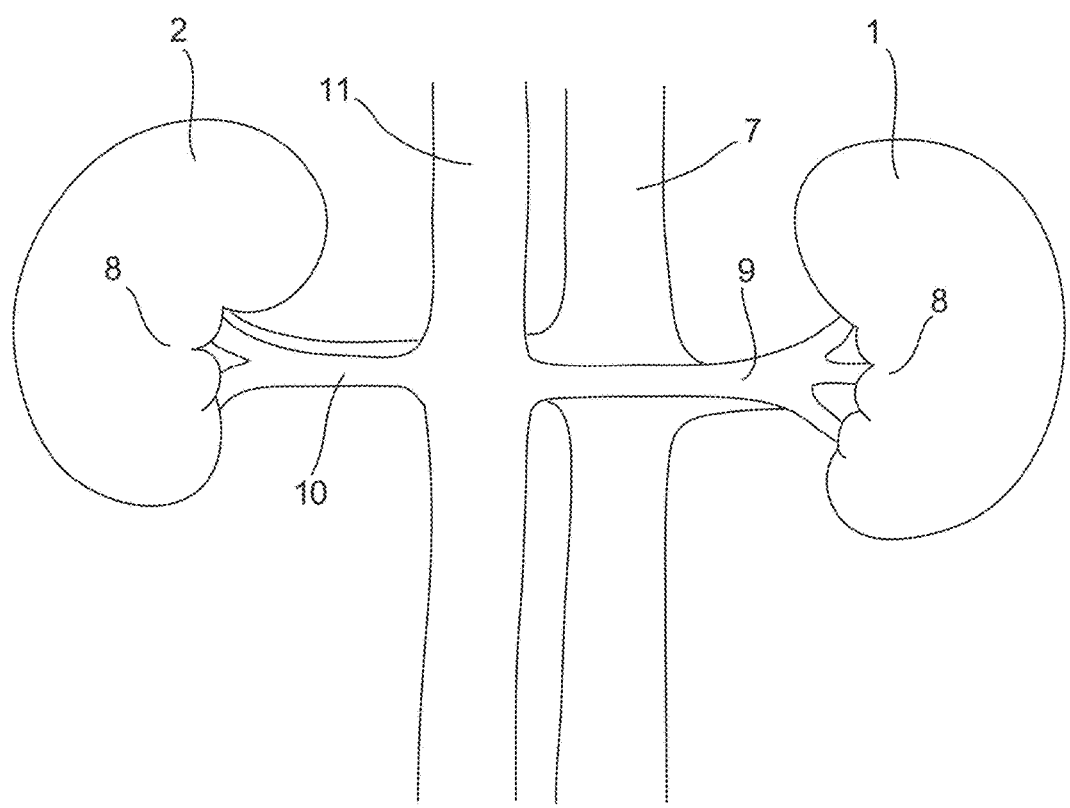
FIG. 2 is a posterior view of human kidneys and supporting vasculature.

FIG. 1 is an anterior view illustration of the kidneys and major arteries and veins supporting the kidneys. The right kidney 1 and left kidney 2 are bean-shaped organs, each approximately the size of a tightly clenched fist. They lie on the posterior abdominal wall behind the peritoneum and on either side of the vertebral column while the superior pole of each kidney is protected by the rib cage. A fibrous connective tissue renal capsule 3 surrounds each kidney and around the capsule is a dense deposit of adipose tissue, the renal fat pad (not shown), which protects the kidney and supporting vasculature. On the medial side of each kidney is a relatively small area called the hilum 4 where the renal artery and the nerves enter and the renal vein and the ureter (not shown) exit. The right renal vein 5 and left renal vein 6 branches off the inferior vena cava 7 and enters the renal sinus 8 of each kidney. Renal veins are blood vessels that carry deoxygenated blood out of the kidney to the inferior vena cava 7. FIG. 2 is a posterior view illustration of the kidneys and major arteries and veins supporting the kidneys. The right renal artery 9 and left renal artery 10 branches off the abdominal aorta 11 and enter the renal sinus 8 of each kidney. The renal arteries carry a large portion of total blood flow to the kidneys. Up to a third of total cardiac output can pass through the renal arteries to be filtered by the kidneys.

Figure 3:
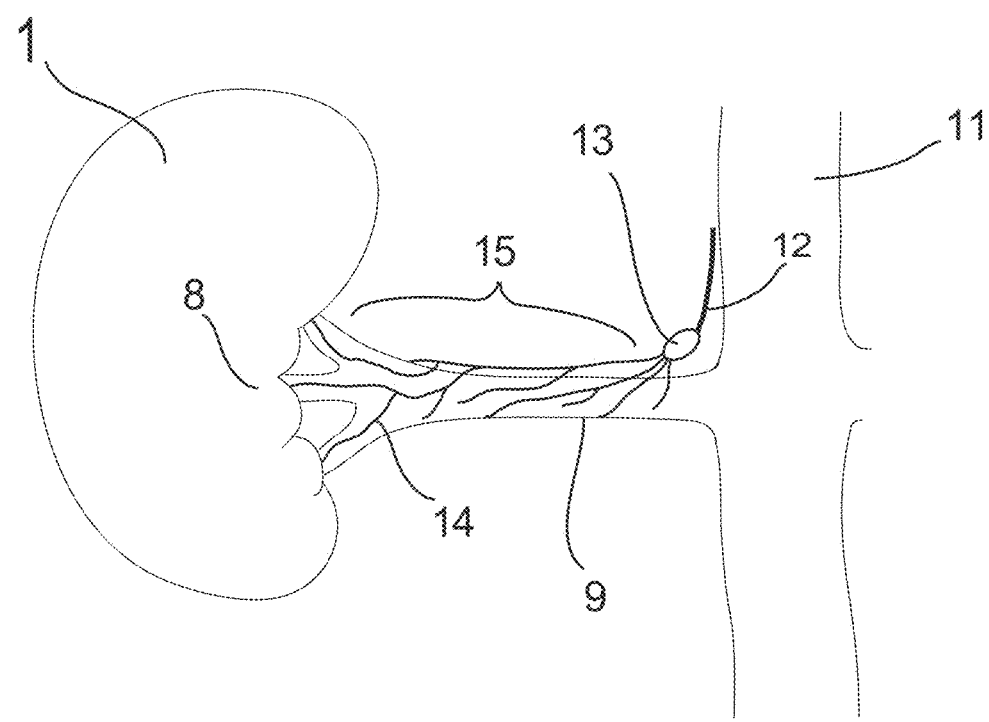
FIG. 3 is an anterior view of the innervation of the right kidney.

FIG. 3 is an anterior view illustration of the right kidney 1 and right renal artery 9 with the renal vein and inferior vena cava removed. The lesser and least thoracic splanchnic nerves 12 originate in the spinal cord and travel to the aorticorenal ganglion 13 which is located at the origin of the renal artery 9 from the abdominal aorta 11. Postganglionic axons 14 then form the renal plexus 15, as this dense network of nerve fibers is often referred to, which runs alongside the renal artery and enters the hilum 4 of the kidney 1. Thereafter, they divide into smaller nerve bundles following the blood vessels and penetrate cortical and juxtamedullary areas.

A ganglion is typically known as a mass of tissue formed by ganglion cells. Ganglia can provide relay points and intermediary connections between different neurological structures in the body, such as the peripheral and central nervous systems. There is typically one aorticorenal ganglion 13 for each renal plexus (2 per human) and it can be located superior, anterior and inferior to the renal artery. Its size can vary from a small swelling approximately 1 mm in diameter to an irregular shape approximately 10 mm long and 5 mm wide.

Percutaneous aorticorenal ganglion modification may be accomplished by delivery of energy to a tissue modifying element located at the distal end of the catheter using an external energy source. Transmission of the energy to the tissue modifying element may be accomplished by various means including transmission through an energy transmitting conduit located within a catheter body that extends the length to the proximal end of the catheter body. Proximal end of catheter body may be coupled by way of connectors and/or cables to external energy source. For example, FIG. 4A is a schematic of an aorticorenal ganglion modifying system utilizing radiofrequency energy. Aorticorenal ganglion modifying catheter 16a comprises an elongated body 17 extending longitudinally between a proximal end and a distal end along a longitudinal axis and comprising an electrode as the tissue modify element 18 located approximately at the distal end of the catheter. Tissue modifying element 18 utilizing an electric current for operation can be manufactured from any electrically conductive material such as stainless steel, copper, Elgiloy™, MP35N, platinum, titanium, Nitinol and various other materials and alloys.

Figure 4B:
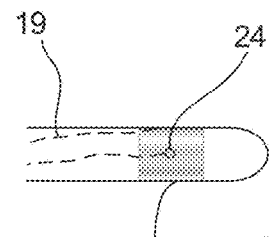
FIGS. 4a and 4b are schematic views of a radiofrequency energy aorticorenal ganglion modifying system.
Figure 4A:
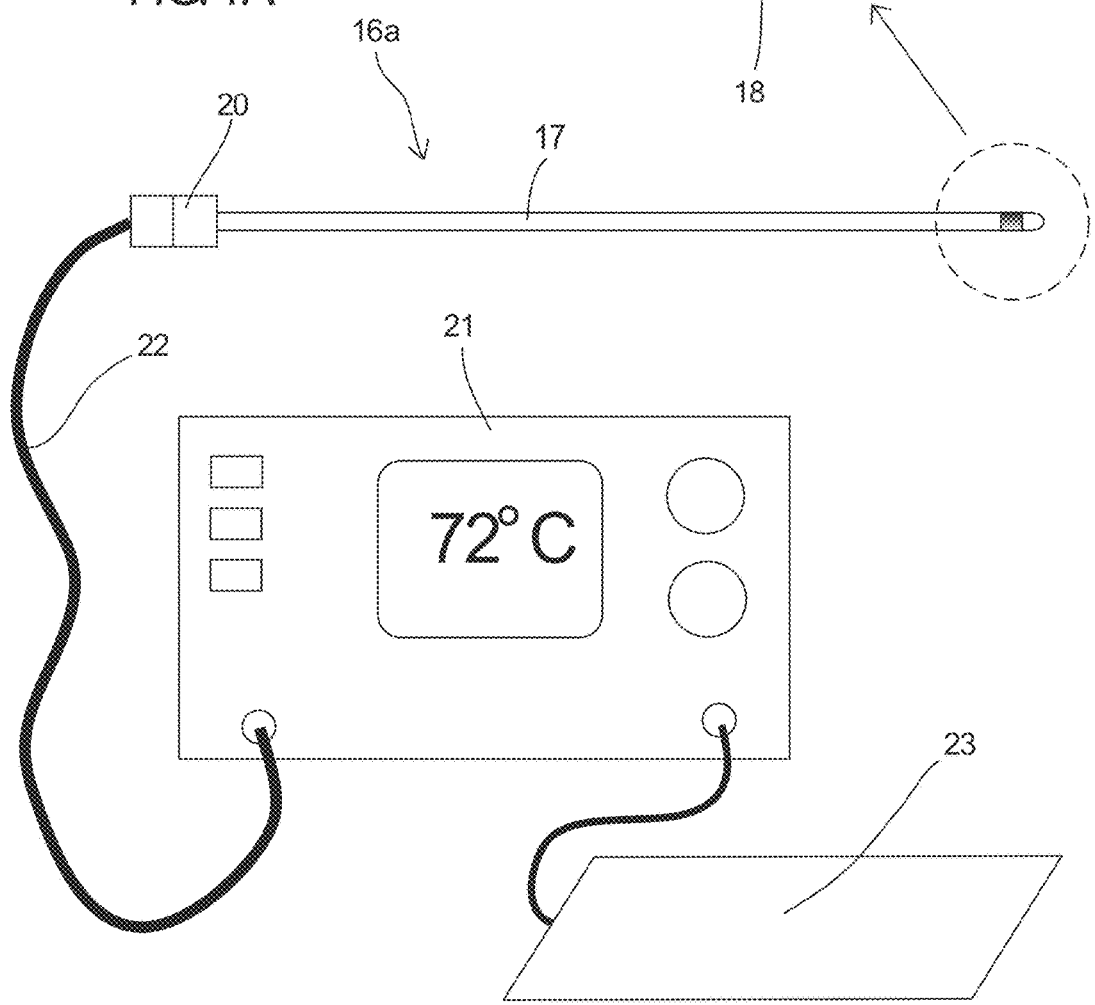

Referring to FIG. 4B, a close up view of the distal end of the catheter shows the electrode 18 with conductor wire 19 attached to the electrode. Conductor wire is located within the catheter body 17 and extends the length to the proximal end of the catheter body and is attached to the electrical connector 20. External energy source (e.g. control box 21) is coupled to the electrical connector by control cord 22 and is also coupled to dispersive electrode pad 23 in a monopolar system. FIG. 4a also shows a tissue sensor element 24 located at the distal end of the catheter. Tissue sensor element can be used to directly detect targeted tissue with well-known technologies such as impedance tissue measurement and temperature measurements. For example element may be designed as an electromyogram (EMG) element that measures the electrical activity of the ganglia and nerves. Tissue sensor element can also be a thermocouple or thermistor and used to monitor and/or control the delivery of RF energy by measuring temperature of the electrode or targeted tissue during activation. In use, electrode pad 23 is attached to the patient's skin and electrode 18 is adjacent targeted tissue (aorticorenal ganglion) creating a closed electrical circuit. When activated, radiofrequency energy travels through targeted tissue resulting in tissue ablation and modification of the aorticorenal ganglion. Aorticorenal ganglion modifying catheter 16a may also be designed as an RF bipolar device by placement of more than one isolated (not in series) electrodes 18 located approximately at the distal end of the catheter. A closed electrical circuit occurs between electrosurgical generator 21 and electrodes 18 when in tissue contact (electrode pad is not required).

Radiofrequency parameters for tissue modification include frequencies between 10 to 800 kHz with a range of 450 to 500 kHz preferred and power between 0.1 to 100 watts with a range of 2 to 10 watts preferred. Applied power control can be achieved by adjusting voltage applied to the RF tissue modifying element (power control), or by adjusting power depending upon tissue impedance measured by the tissue modifying element (impedance control) or by adjusting the power to keep the tissue modifying element containing a thermocouple or thermistor at a defined target value (temperature control). Temperature control can be in the range of 40-100° C. for a period of 5 seconds to 5 minutes. Preferably, the temperature range is 60-80° C. for a period of 60 to 90 seconds. Temperature control mechanism may also utilize a control feedback mechanism such as a proportional-integral-derivative (PID) controller or combination thereof (e.g. PI, PD controllers) to maintain target temperatures during power delivery. Aorticorenal ganglion modifying catheter employing ultrasound energy for tissue modification may utilize a piezo-electric crystal as the tissue modifying element and be coupled to external energy source as previously described. Ultrasound energy in the range of 10 KHz to 4 MHz may be applied to affect tissue modification. Aorticorenal ganglion modifying catheter may also utilize microwave energy which employs electromagnetic waves in the microwave spectrum (300 MHz to 300 GHz) for tissue modification.

Figure 5:
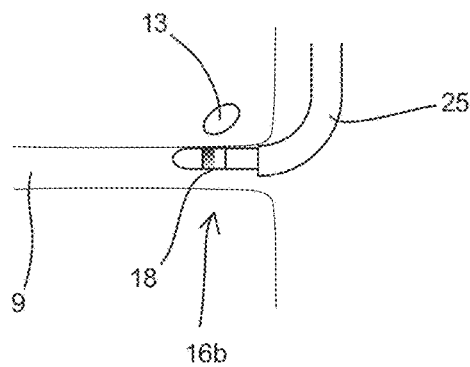
FIG. 5 is a close up view of the monopolar aorticorenal ganglion modifying catheter located in the renal artery.

Percutaneous placement of the aorticorenal ganglion modifying catheter in proximity to the aorticorenal ganglion may be accomplished using any of the currently available techniques and ancillary equipment for vascular interventions including guided sheaths, steerable distal tip assemblies and over the wire configurations employed for diagnostic and therapeutic devices. FIG. 5 is a close up view of the monopolar radiofrequency aorticorenal ganglion modifying catheter 16b placed within a guide sheath 25 and positioned within the renal artery 9 so that tissue modifying element 18 is adjacent the aorticorenal ganglion 13.

Figure 6:
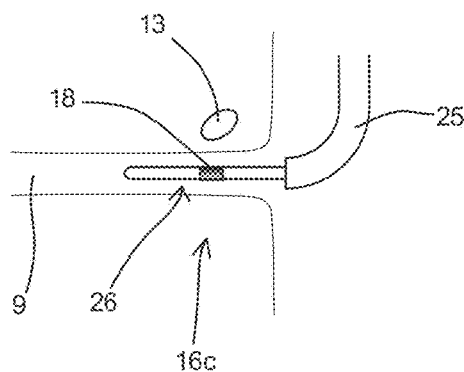
FIG. 6a-6c is a close up view of the balloon aorticorenal ganglion modifying catheter located in the renal artery.
Figure 6:
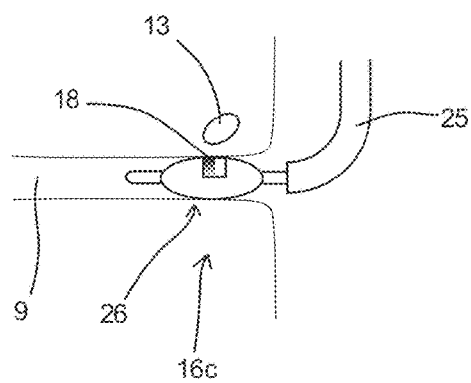

FIG. 6 is an illustration of the distal end of an aorticorenal ganglion modifying catheter assembly 16c comprising balloon element assembly 26 and tissue modifying element 18 attached to outer surface of balloon element assembly positioned within the renal artery 9. Balloon element assembly 26 is similar in design to the balloons manufactured for coronary angioplasty catheters. Balloon element may be manufactured with a relatively thin walled compliant or noncompliant plastic. Examples of materials used to manufacture the balloon element include polyethylene, polyethylene terephthalate, nylon and silicone elastomers. Balloon element assembly 26 is attached to an inflation tube (not shown) which extends longitudinally between proximal end and distal end of the catheter body 17. Balloon element assembly 26 is movable between a collapsed configuration and an expanded configuration, as shown in FIG. 6b. Balloon element assembly 26 may be inflated and deflated similarly to techniques used for angioplasty, for example by use of a pneumatic indeflator attached to the proximal end of inflation tube. In use, balloon element assembly 26 is placed at targeted treatment site within vessel lumen and inflated until electrode element 18 is contacting the vessel wall adjacent the aorticorenal ganglion 13. Tissue modification with balloon aorticorenal ganglion modifying catheter is performed similarly as described with monopolar aorticorenal ganglion modifying catheter.

Figure 7:
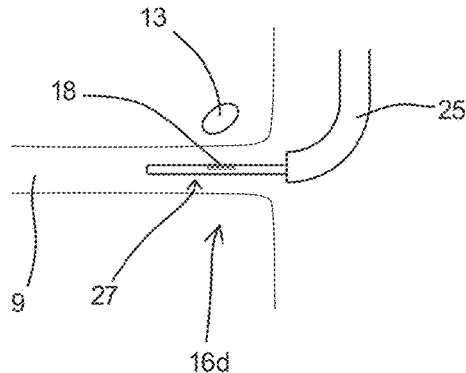
FIG. 7a-7c is a close up view of the basket aorticorenal ganglion modifying catheter located in the renal artery.
Figure 7:
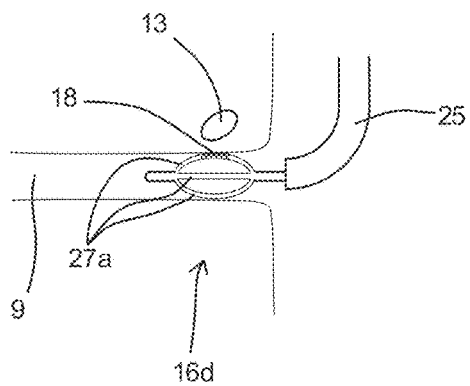

A similar device 16d to the catheter assembly 16c of FIG. 6 is illustrated in FIG. 7a-c. Balloon element assembly 26 is replaced with a basket or malecot element assembly 27. Basket element assembly comprises thin rib members 27a of solid deformable material and tissue modifying element 18 attached to the outer surface of ribbon. Basket element assembly 27 is movable between a collapsed arrangement (FIG. 7a) and an expanded arrangement (FIG. 7b) with the intermediate segments of the ribbons 28 in the expanded arrangement moving laterally outward relative to the distal and proximal ends of the ribbons 28 with respect to the collapsed arrangement of FIG. 7a. Basket element assembly 27 can be expanded or collapsed by various means. One example involves manufacturing ribbons with a memory metallic alloy (e.g. Nitinol) which have a preformed expanded shape that is constrained in a catheter lumen and then allowed to recover to preformed shape upon exit of the catheter lumen. Another example involves mechanical expansion employing pull wire. Pull wire (not shown) is an elongated body extending longitudinally between a proximal end and a distal end, slidably contained within catheter body. Distal end of pull wire is attached to distal ribbon 28 ends and proximal ribbon ends are fixed to the catheter body. Basket element assembly 27 expansion occurs when pull wire is moved in a proximal and longitudinal direction relative to the catheter body causing proximal ribbon ends and distal ribbon ends to converge resulting in radially outward expansion of intermediate portion of ribbons 28.

In use, aorticorenal ganglion modifying catheter 16d containing basket element assembly 27 is inserted into targeted treatment site within vessel lumen 9 in the collapsed arrangement (FIG. 7a). Basket element assembly 27 is expanded and ceases expansion once significant resistance occurs between intermediate ribbon segments 28 and the inner vessel lumen surface (FIG. 7b). Tissue modification with basket aorticorenal ganglion modifying catheter is performed similarly as described with monopolar aorticorenal ganglion modifying catheter.

Figure 8:
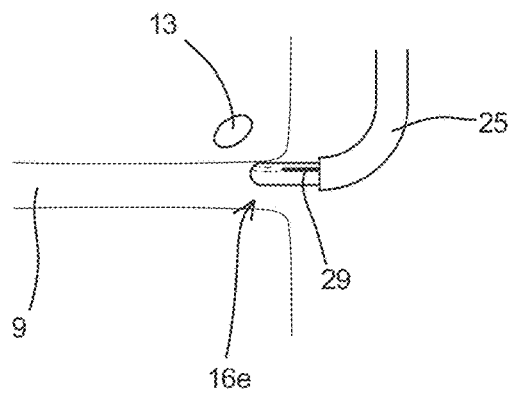
FIGS. 8a and 8b is a close up view of the needle electrode aorticorenal ganglion modifying catheter located in the renal artery.
Figure 8:
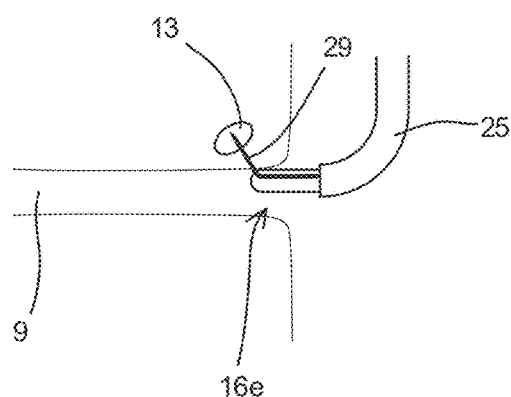
Figure 6:
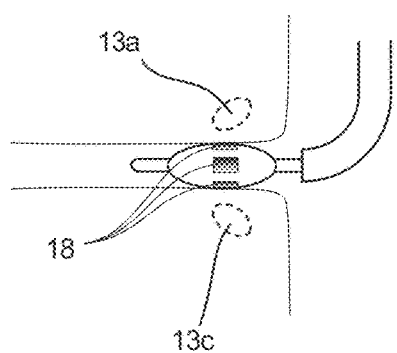
Figure 7:
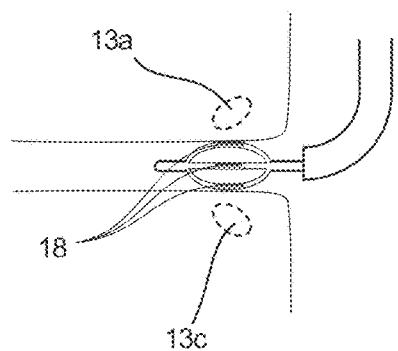

FIGS. 8a and 8b are an illustration of the distal end of an aorticorenal ganglion modifying catheter assembly 16e comprising a tissue modifying element in the form of a needle electrode 29 positioned within the renal artery 9. The needle electrode element 29 is a typically rigid or semi-ride longitudinal cylindrical structure slidably contained within catheter body comprising a sharp pointed distal end to aid with insertion into vessel wall and proximal end coupled electrically to electrical connector and attached mechanically to needle advancing mechanism (not shown). Needle electrode element 29 can be advanced or retracted by the operator by various means including wires, hand held mechanisms and handles with activation mechanism.

In use, aorticorenal ganglion modifying catheter 16 containing needle electrode element 29 is inserted into targeted treatment site within vessel lumen 9 with needle electrode element retracted within catheter body (FIG. 8a). Needle electrode element 29 is advanced from distal end of catheter and pierced and inserted into the vessel wall in proximity to the aorticorenal ganglion 13 (FIG. 8b). Tissue modification with electrode needle aorticorenal ganglion modifying catheter is performed similarly as described with monopolar aorticorenal ganglion modifying catheter. It may be desirable to control the insertion depth of the needles to accurately target the renal nerves and prevent any undesired damage to deeper tissues. Various techniques and mechanisms can be employed to control the insertion depth of the needle into the vessel wall such as adding mechanical stoppers to the needle electrode element 29. Needle element can also be designed as a hypodermic needle so that pharmacological, chemical, sclerosing, radiopaque markers, anesthetics and fluids can be delivered to tissue approximate the aorticorenal ganglion 13. Needle electrode element can also contain tissue sensor elements 24 to assist in monitoring and controlling energy delivery as well as direct detection of the aorticorenal ganglion 13 (e.g. impedance tissue measurements).

Figure 9:
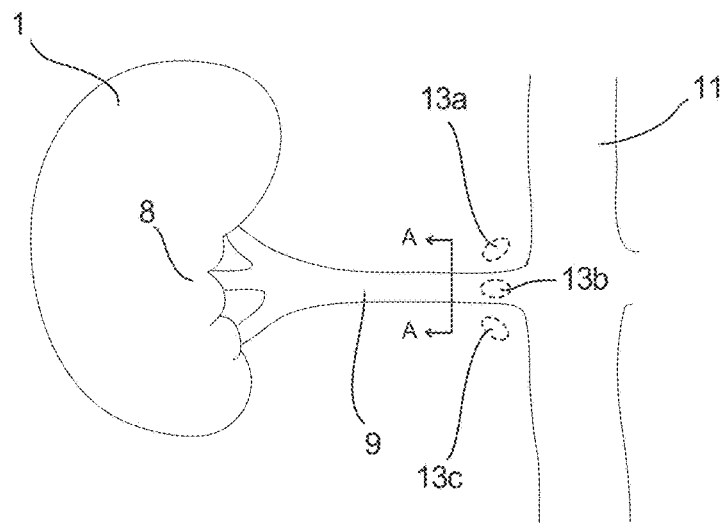
FIGS. 9a and 9b is an anterior and sagittal view of the right aorticorenal ganglion.
Figure 9:
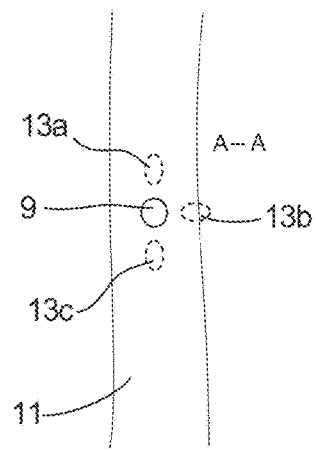
Figure 10:
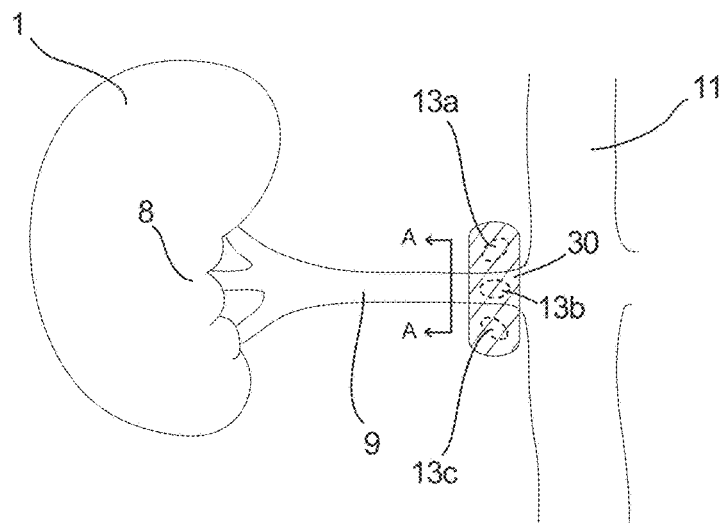
FIGS. 10a and 10b is an anterior and sagittal view of the right aorticorenal ganglion contained within a tissue modification zone.
Figure 10:
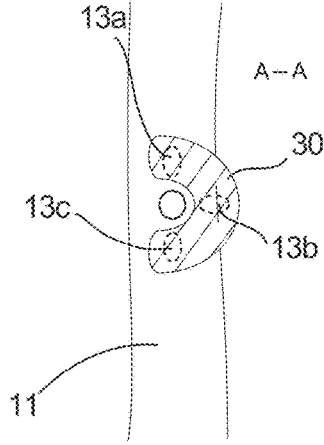

Typically, there is one aorticorenal ganglion 13 associated with each kidney 1 and is either located superior 13a, anterior 13b or inferior 13c to renal artery 9 as shown in the anterior view of FIG. 9a and sagittal view in FIG. 9b. One method of treatment involves creating tissue modification (e.g. tissue ablation when radiofrequency energy is employed) in the anatomic regions containing the aorticorenal ganglion 13. FIGS. 10a and 10b show a tissue modification zone 30 in the shape of a half toroid or half doughnut. Lesion shape can be contiguous or contain discrete segments that generally look similar to a half toroid.

Half toroid shaped lesions can be created with previously disclosed embodiments of the current invention. One method involves percutaneous placement and treatment with the monopolar radiofrequency aorticorenal ganglion modifying catheter in discrete segments along the vessel. For example, radiofrequency electrode element can be repositioned for tissue contact and activated in a superior, anterior and inferior position with the renal artery adjacent the aorticorenal ganglion. Shape of tissue modification (e.g. lesion) will generally look similar to a half toroid.

Half toroid shaped lesions can also be created with various design modifications of the previously disclosed embodiments. FIGS. 6c and 7c show the balloon and basket aorticorenal ganglion modifying catheter 16 respectively, with multiple electrode elements 18. Electrode elements are positioned in a superior, anterior and inferior configuration to create a half toroid shaped lesion capturing the aorticorenal ganglion when activated.

Well known radiographic technologies may be utilized to locate aorticorenal ganglia for treatment including intravascular and external ultrasound, magnetic resonance imaging (MRI), electromyography (EMG), nerve conduction velocity testing (NCV), somatosensory evoked potential (SSEP) and x-ray computed tomography (CT scan) and may be incorporated into the aorticorenal ganglion modifying catheter 16

Aorticorenal ganglion and/or renal nerves (e.g., the postganglionic nerves 14 located between the ganglion 13 and the kidney 1) can be detected by stimulation with a tissue stimulating element and measurement of a physiological response with a physiological measurement element. Tissue stimulating element and/or physiological measurement element can be separate catheters or incorporated as elements into aorticorenal ganglion modifying catheter. Physiological measurement element (sensor) located approximately at the distal end of the catheter may function by transmitting data collected at the sensor to an external system for analysis. Transmission of data may be accomplished by various means including delivering a signal from sensor through a signal transmitting conduit located within the catheter body that extends the length to the proximal end of the catheter body. Proximal end of catheter body is coupled by way of connectors and/or cables to system, to a software containing system for analysis. For example a pressure sensor, such as a pressure transducer, located at the distal end of the catheter transmits electrical data from sensor through the catheter body to system for analysis.

Physiological data may be analyzed by software for determining ganglion location and treatment verification by various means. One method of determining ganglion location involves comparing non-stimulated tissue physiological data to stimulated tissue physiological data with pre-set limits established to ascertain positive and negative results for ganglion detection. For example, when intravascular Doppler ultrasound is utilized for physiological response, blood flow velocity measured as centimeters per second would decrease significantly when ganglion is stimulated due to renal vasoconstriction compared non ganglionic tissue stimulation.

Figure 11:
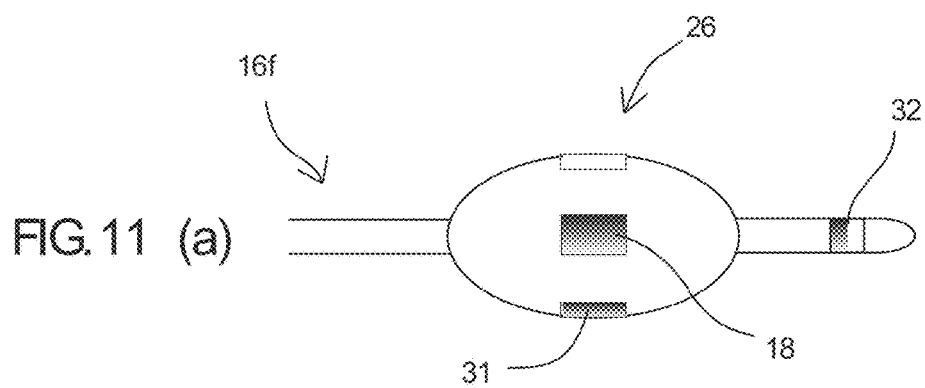
FIG. 11a-11c is a schematic of the balloon aorticorenal ganglion detection and modifying system.
Figure 11:
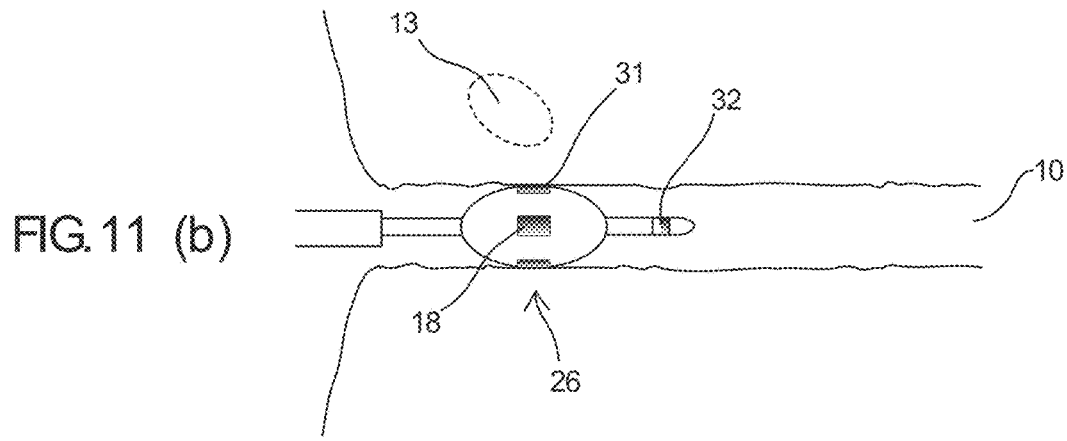
Figure 11:
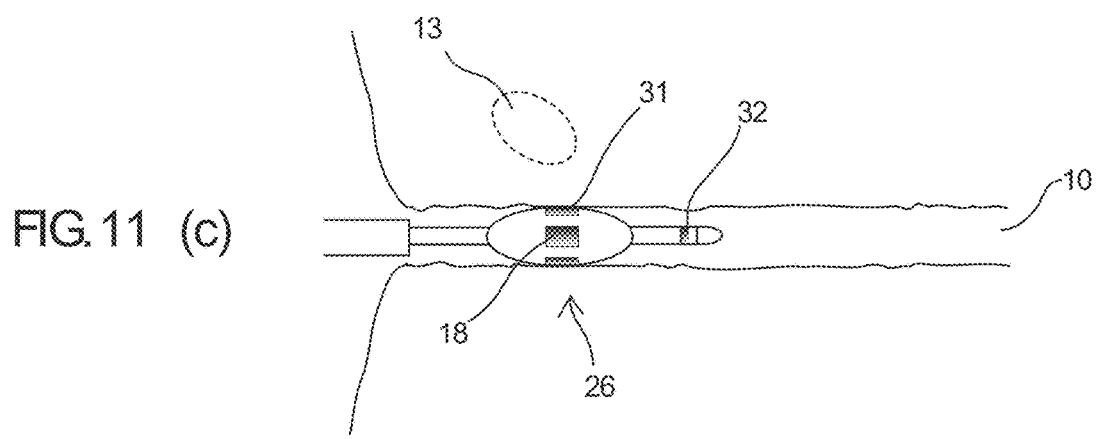

FIG. 11(a) is a close up view of the distal end of an aorticorenal ganglion modifying catheter 16f that is capable of stimulation, sensing, and modifying tissue. The catheter comprises a balloon element assembly 26 having a tissue stimulating element 31, a sensing or physiological measurement element 32, and a tissue modifying element 18.

The tissue stimulating element 31 which utilizes electrical current for operation can be manufactured from any electrically conductive material such as stainless steel, copper, Elgiloy™, MP35N, platinum, titanium, Nitinol and various other materials, and alloys. Similar materials may also be used as tissue modifying element 18. The physiological measurement element 32 comprises a sensor or sensors such as a pressure transducer, ultrasound transducer, optical coherence tomography sensor, temperature sensors and the like. The tissue modifying element, tissue stimulating element and physiological measurement element may also be comprised of a nanoelectronic, flexible electronic, flexible sensor, microsensor, stretchable electronic and the like. FIG. 11(b) is an illustration of the distal end of the aforementioned catheter positioned within the renal artery 10 before the application of electrical stimulation. Preferably, the catheter 16f is connected to and operated via a control box 21, as described in detail elsewhere in this specification.

FIG. 11(c) is an illustration of the physiological response of renal vasoconstriction during stimulation with tissue stimulating element 31. The reduction in inner luminal diameter of the vessel is detected by sensor 32 (e.g. measurement of diameter change with ultrasound transducer or blood pressure measurement) and/or is detected under fluoroscopy by observing radially converging radiopaque tissue stimulating elements 31.

Figure 12:
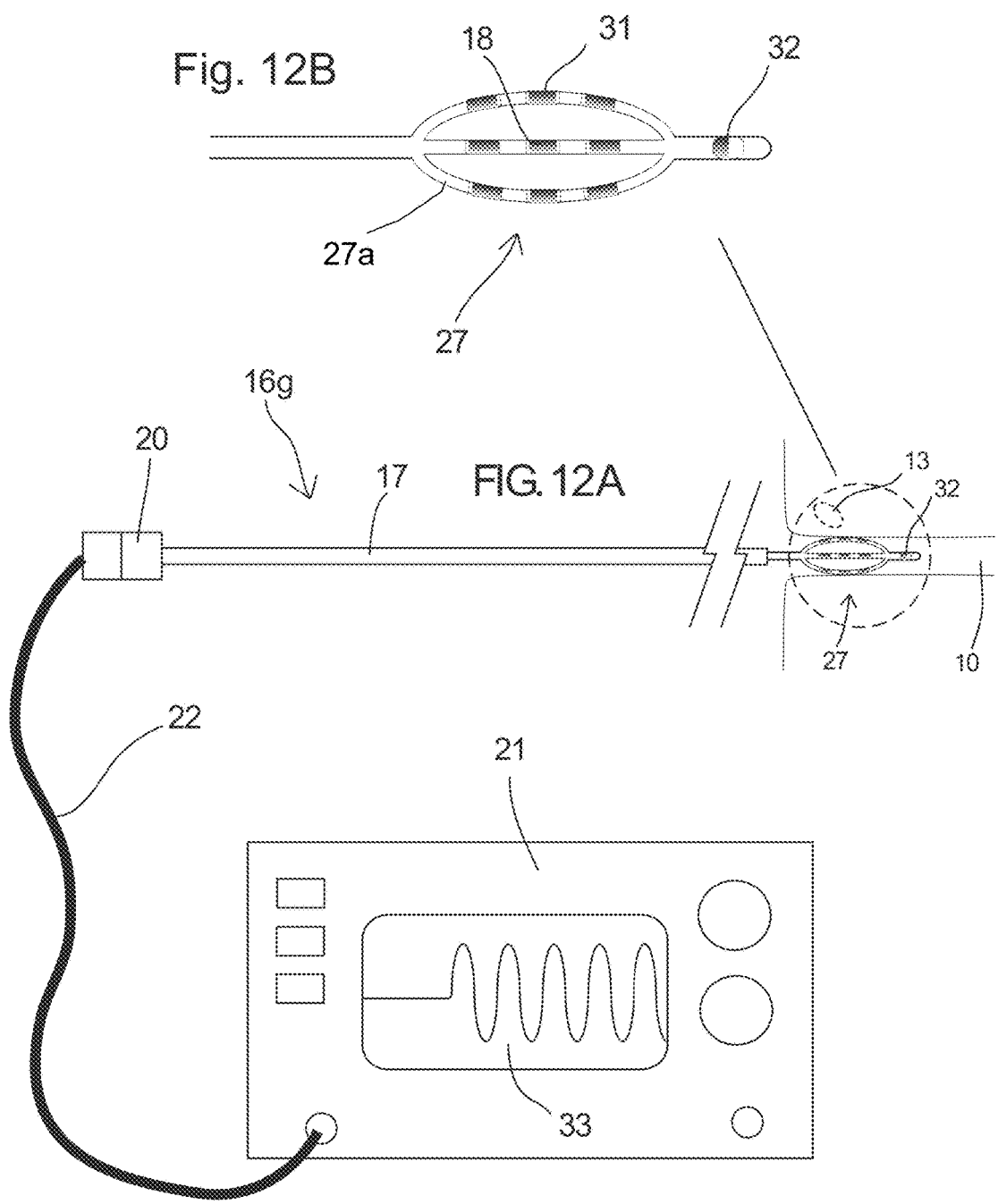
FIGS. 12a and 12b are schematic views of the basket aorticorenal ganglion detection and modifying system.

FIGS. 12a and 12b are schematic views of an aorticorenal ganglion modifying catheter 16g that is capable of stimulation, sensing, and modifying tissue. Specifically, the catheter 16g comprises a distal basket element assembly 27 including tissue modifying elements 18, tissue stimulating elements 31, and sensor 32. The basket element assembly 27 can be formed from a plurality of rib member 27a (e.g., between 3 and 10 rib members 27a) and can be configured to radially expand from a compressed configuration via a manual expansion mechanism (e.g., a control wire) or via self-expansion (e.g., superelastic shape memory material).

Each rib 27a of the basket 27 can include at least one stimulating element 31 and one modifying element 18, and more preferably, several of each elements on each rib. Preferably, the sensor 32 is located distally and spaced apart from the elements 18 and 31, however, in an alternate embodiment, one or more sensors 32 can also be located on the ribs of the basket 27. It should also be understood that while a basket 27 is described, any number of shapes and materials can be used, such as a spiral or coil shape, a tubular shape, or a balloon.

While it is contemplated that all of the stimulating elements 31 can be activated in unison and all of the modifying elements 18 can be activated in unison, less than all of each group of elements can also be activated to allow the location of the aorticorenal ganglion to be better targeted (e.g., radially and axially). For example, the control box 21 (either manually or automatically) may initially only activate the stimulating elements 31 on one or two ribs of the basket 27 at a time, allowing the user or software in the control box 21 to determine the rib 27a closest to the aorticorenal ganglion 13. In another example, the software in the control box 21 may activate and deactivate the stimulating elements 31 in a predetermined pattern, such as consecutive, adjacent ribs. In another example, the user or software in the control box 21 can activate all of the proximal, distal, of middle sensors of each group, allowing the user or control box 21 to determine if the aorticorenal ganglion is located proximally, distally, or immediately adjacent to the basket 27. In yet another example, any combination of the above described element activation can be used (e.g., only the distal stimulating elements 31 on a single rib 27a of the basket 27 can be activated.

The control box 21 preferably includes controls and a visual display 33 to provide information to the user, such as a measured physiological response (e.g., blood pressure data from sensor 32) or status of any of the elements (e.g., whether the tissue modification element 18 is turned on). In one embodiment, the visual display 33 is a touch screen. Additionally, the control box 21 includes software configured to operate the components on the catheter 16g, display simple data points or stream real time data, and also provided visual and audible procedure instructions during operation. The control box software may also control the catheter to prevent certain undesired modes of operation, and to control operation of the catheter in the event of an interruption in proper operation. While the control box 21 is depicted as a separate, standalone unit, it is also contemplated that it could be incorporated into the handle or proximal end of the any of the catheters described in this specification.

In operation, the distal end of catheter 16g is positioned within the renal artery 10 (or alternately in the renal vein 5) and proximal end of the catheter 16g is connected to the control box 21 via the control cord 22. Next, the user interfaces with the control box 21 to begin a stimulation and sensing routine. As previously discussed, such a routine may include sensing with the sensing element 32 while all of the stimulating elements 31 are activated or while only select portions are activated (e.g., elements 31 on only a single rib 27a and/or in the proximal, middle, or distal portions).

Once the sensor element 32 and control box 21 detect and display the appropriate change in physiological data (e.g., blood pressure pulsation), the modification elements 18 (or a portion thereof), are activated. This activation can be manually activated on the control box 21 by the user or automatically performed by the software in the control box 21 based on the data from the sensing elements 32.

Finally, the stimulating elements 31 and sensing element 32 are again activated (or optionally are continually activated during the entire process) to allow confirmation that the aorticorenal ganglion (or possibly another renal nerve location) has been treated to adequately limit or prevent nerve signals from reaching the kidney. Again, this confirmation may be performed manually by the user by looking at data on the visual display 33 or automatically by the software of the control box 21 (which may further indicate confirmation via an audible and/or visual signal). While this process of use was described in connection with catheter 16g, it should be understood that any of the other embodiments described in this specification can be used in a similar fashion (e.g., alone for a catheter having stimulating, sensing and modification elements, or several different catheters that each contain one or more of these elements).

Figure 13:
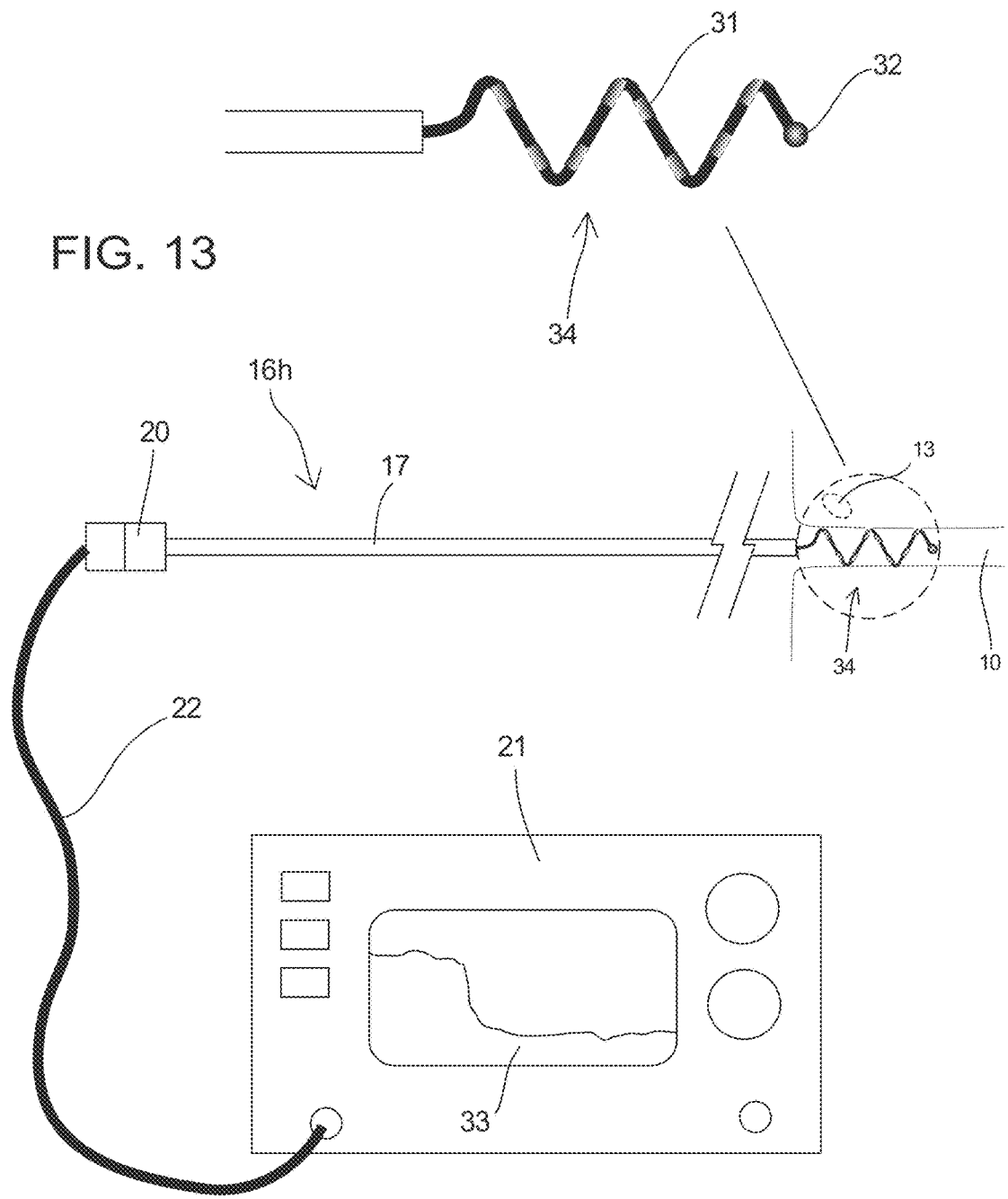
FIG. 13 is a schematic of the coil aorticorenal ganglion detection and modifying system.

FIG. 13 is a schematic of the aorticorenal ganglion modifying catheter 16h comprising a distal coil element assembly 34 comprising tissue stimulating elements 31 and sensor 32. Distal end of catheter 16h is positioned within the renal artery 10 and proximal end of the catheter is connected to a control box 21 comprising a visual display 33. In use, visual display shows the operator a detected response, for example during stimulation of the aorticorenal ganglion with stimulating element 31, blood flow velocity can be detected with sensor 32 comprising a Doppler ultrasound transducer and exhibited on control box visual display 33.

Aorticorenal modifying catheter may also comprise a lumen within the catheter body that extends from distal end to proximal end of the catheter body. Catheter lumen allows for slidable placement of a guide wire which is used to assist with placement in the renal vasculature as commonly performed for percutaneous procedures utilizing a guide wire. Catheter lumen may be designed for rapid exchange of multiple catheters with a stationary guide wire by various means for example by comprising a radial slit from the lumen to the outside surface of the catheter body that extends longitudinally approximately half the length of the catheter. Lumen may also be used for placement of tissue stimulating element and physiological measurement element (e.g. FloWire® Doppler Guide Wire and Verrata™ Pressure Guide Wire).

Stimulating element and tissue modifying element may be activated separately or simultaneously with the latter allowing for a cessation of tissue modification once acceptable nerve disruption, as measured by a physiological response, is achieved. Stimulating element utilizing radiofrequency energy may be a monopolar or bipolar arrangement, connected to an external electrical stimulator or electrosurgical generator capable of delivering adequate electrical parameters for ganglion or nerve stimulation. Nerve stimulation may be achieved with frequencies between 0.1 to 100 Hz with a range of 2 to 50 Hz preferred, voltage between 0.1 to 30 volts with a range of 5 to 15 volts preferred and pulse duration between 0.1 to 10 ms with a range of 0.2 to 5 ms preferred. One set of stimulation energy parameters or variation of parameters may be utilized for tissue stimulation. For example, lower frequencies (e.g. 2 Hz) may be used to detect efferent nerve physiological responses and higher frequencies (e.g. 50 Hz) may be used to detect afferent nerve physiological responses. Frequency modulation may occur in series, parallel, simultaneously, as a slope function or step function or any combination thereof. Voltage, current and pulse duration may also be varied during stimulation to achieve desired physiological responses of the ganglia and nerve tissue. A single control box may be used for tissue stimulation, physiological response analysis and tissue modification.

While the stimulating elements 31 and the tissue modifying elements 18 in any of the embodiments of this specification may be separate, dedicated electrodes (i.e., only used for one purpose), it is also contemplated that each electrode can operate as either type of electrode. For example, the electrodes may be connected to a current-generating source in the control box 21 that is capable of producing aorticorenal ganglion stimulating current and tissue modifying current (as described elsewhere in this specification).

Figure 14A:
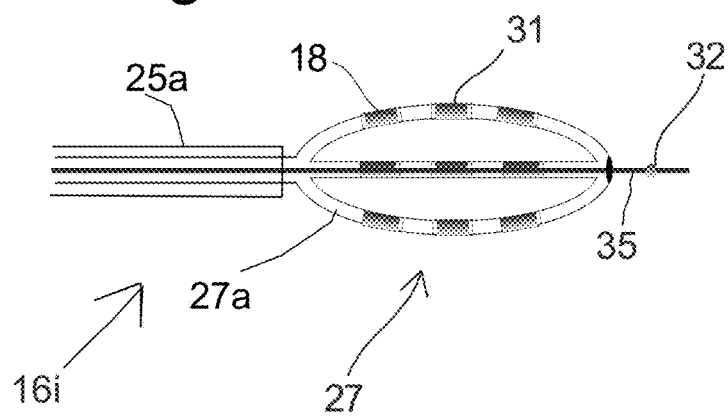
FIGS. 14A and 14B are a schematic view of an aorticorenal ganglion detection and modifying system.
Figure 14B:
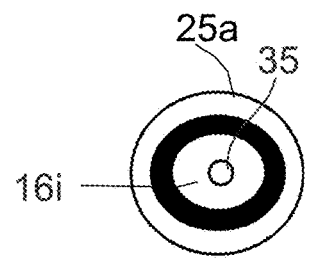
Figure 15A:
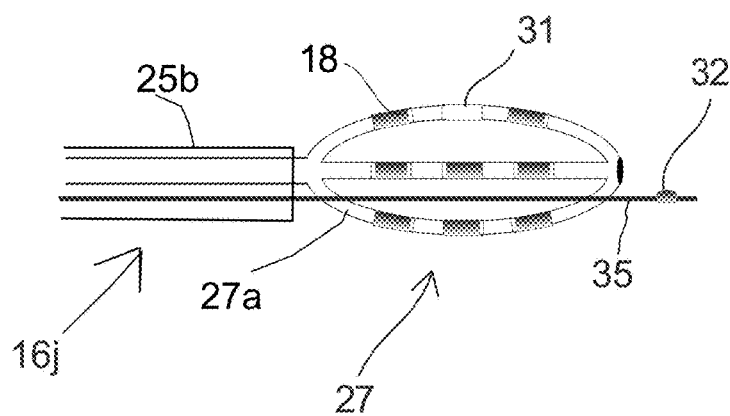
FIGS. 15A and 15B are a schematic view of an aorticorenal ganglion detection and modifying system.
Figure 15B:
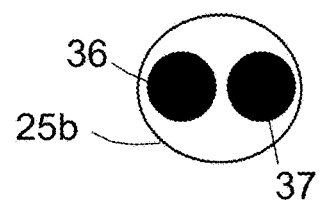

Turning to FIGS. 14A and 14B, an aorticorenal ganglion modifying catheter assembly 16i is illustrated within a single lumen guide sheath 25a. The catheter 16i also includes an interior lumen that opens at the distal end of the basket 27 and the proximal end of the catheter 16i, allowing a separate sensor catheter 35 with sensing element 32 to be separately moved relative to the basket portion 27a. In another embodiment FIGS. 15A and 15B illustrate an aorticorenal ganglion modifying catheter assembly 16J located within a first lumen 36 of a guide sheath 25b and a separate sensor catheter 35 located within a second lumen 37.

Figure 16:
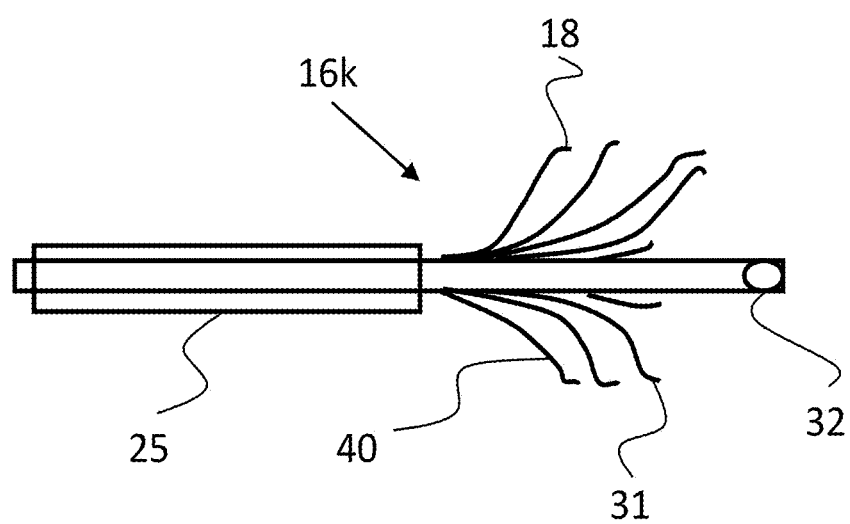
FIG. 16 a schematic view of an aorticorenal ganglion detection and modifying system.

FIG. 16 illustrates another embodiment of an aorticorenal ganglion modifying catheter assembly 16k which is generally similar to the previously described embodiments, but includes a plurality of paddles or arms 40 having on or more of the stimulating elements 31 or the tissue modifying elements 18. Preferably, the arms 40 are composed of superelastic material (e.g., Nitinol) and configured or biased to self-expand radially outward from the main body. In one example, the entire arm 40 includes a conducting material, allowing the entire arm 40 to act as either the stimulating element 31 or the tissue modifying element 18. In another example, the arms 40 may each include a wire or similar conductive path which connects to the stimulating element 31 or the tissue modifying element 18 at its tip.

There are other methods not employing electric current to stimulate ganglia or nerve tissue such as of a chemical or drug that stimulates the targeted tissue. For example, adrenergic drugs stimulate sympathetic nerves by either mimicking the action of the neurotransmitter norepinephrine or stimulating its release. Examples of adrenergic drugs include epinephrine, norepinephrine, isoproterenol, dopamine, dobutamine, phenylpropanolamine, isoetharine, albuterol, terbutaline, ephedrine and xylazine. Drugs can be delivered by various means including by use of previously described hypodermic needle electrode element 29.

Experiment 1

Chronic swine study was performed to demonstrate reduction in renal nerve activity after modification of the aorticorenal ganglia. The domestic swine model is an established model for the renal system because the pig renal anatomy, including circulatory and nervous system, is similar to that of humans.

The procedure involved placing the anesthetized test animal in dorsal recumbency, followed by a 10-cm midline abdominal incision in order to access the renal anatomy. Peritoneum was removed to expose left and right renal artery, vein, aorta and vena cava. Adventitia was stripped from the renal arteries and veins to expose the renal nerve plexus and aorticorenal ganglia. Direct electrical stimulation of the ganglia was performed at 15 volts, 5 Hz and 0.5 msec. pulse duration using a Grass Instruments SD9 Square Pulse Stimulator (Grass Technologies, Warwick, R.I.). Proper identification of the aorticorenal ganglion was confirmed during stimulation by observation of renal artery constriction and kidney blanching (renal vasoconstriction). Aorticorenal ganglia were surgically removed bilaterally and captured for histopathology and the abdomen sutured in two layers at the conclusion of the surgical excision procedure.

At approximately 7 days, the animals were sacrificed and renal cortical samples were removed for measurement of renal cortex norepinephrine levels. Norepinephrine is a neurotransmitter secreted at the end of nerves and is measured to determine nerve activity and is a surrogate for measuring renal denervation success in animals. Two test animals with histologically confirmed aorticorenal ganglia removal were compared to 2 naïve control animals. Renal norepinephrine was reduced 72% in the test animals compared to the controls.

Experiment 2

Figure 17:
FIG. 17 is a frame capture of a baseline nephrogram.

An acute swine study was performed to evaluate the feasibility of detecting an acute physiological response to percutaneous stimulation of the aorticorenal ganglion and renal nerve tissue. The procedure involved creating percutaneous access to the renal venous and arterial vasculature through a jugular and femoral puncture site of an anesthetized test animal in dorsal recumbency. Guide sheaths used for radiopaque contrast delivery were placed with fluoroscopic guidance in both the left renal vein and left renal artery to perform a baseline nephrogram. FIG. 17 is a frame capture of the baseline nephrogram showing normal intrarenal vessel emptying and kidney perfusion.

Figure 18:
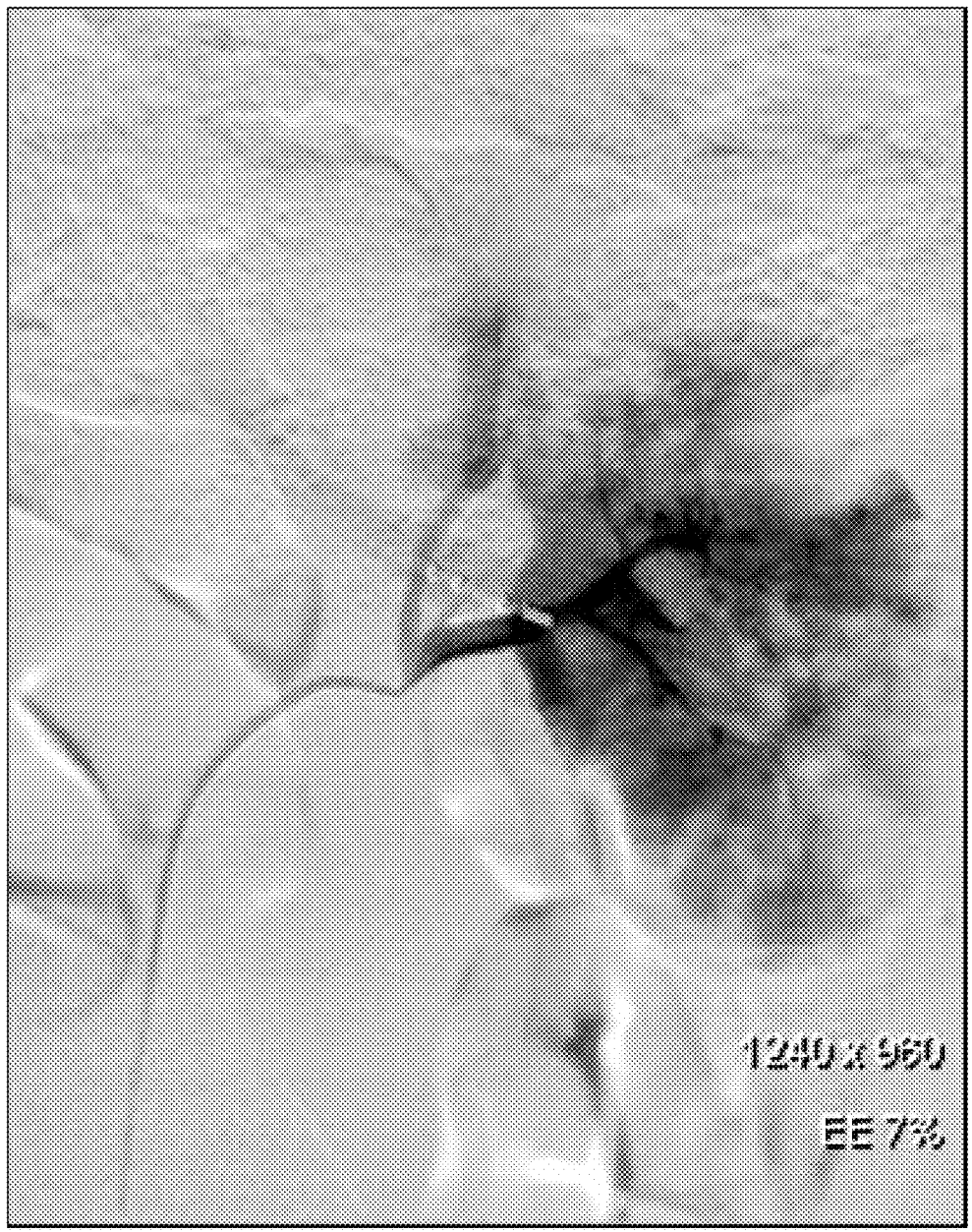
FIG. 18 is a frame capture of a nephrogram performed with stimulation before tissue modification.

A modified electrophysiology catheter (5 French Marinr™ Ablation Catheter, Medtronic, Minneapolis, Minn.) attached to a Grass Instruments SD9 Square Pulse Stimulator (Grass Technologies, Warwick, R.I.) was percutaneously placed in the left renal vein. Direct stimulation of the renal vein wall was performed at 15 volts, 5 Hz and 0.5 msec. pulse duration at several locations simultaneously with contrast delivery to the left renal artery to observe physiological responses. FIG. 18 is a frame capture of a nephrogram performed with stimulation demonstrating activation of the efferent renal sympathetic nerves resulting in renal vasoconstriction and decreased renal blood flow.

Figure 19:
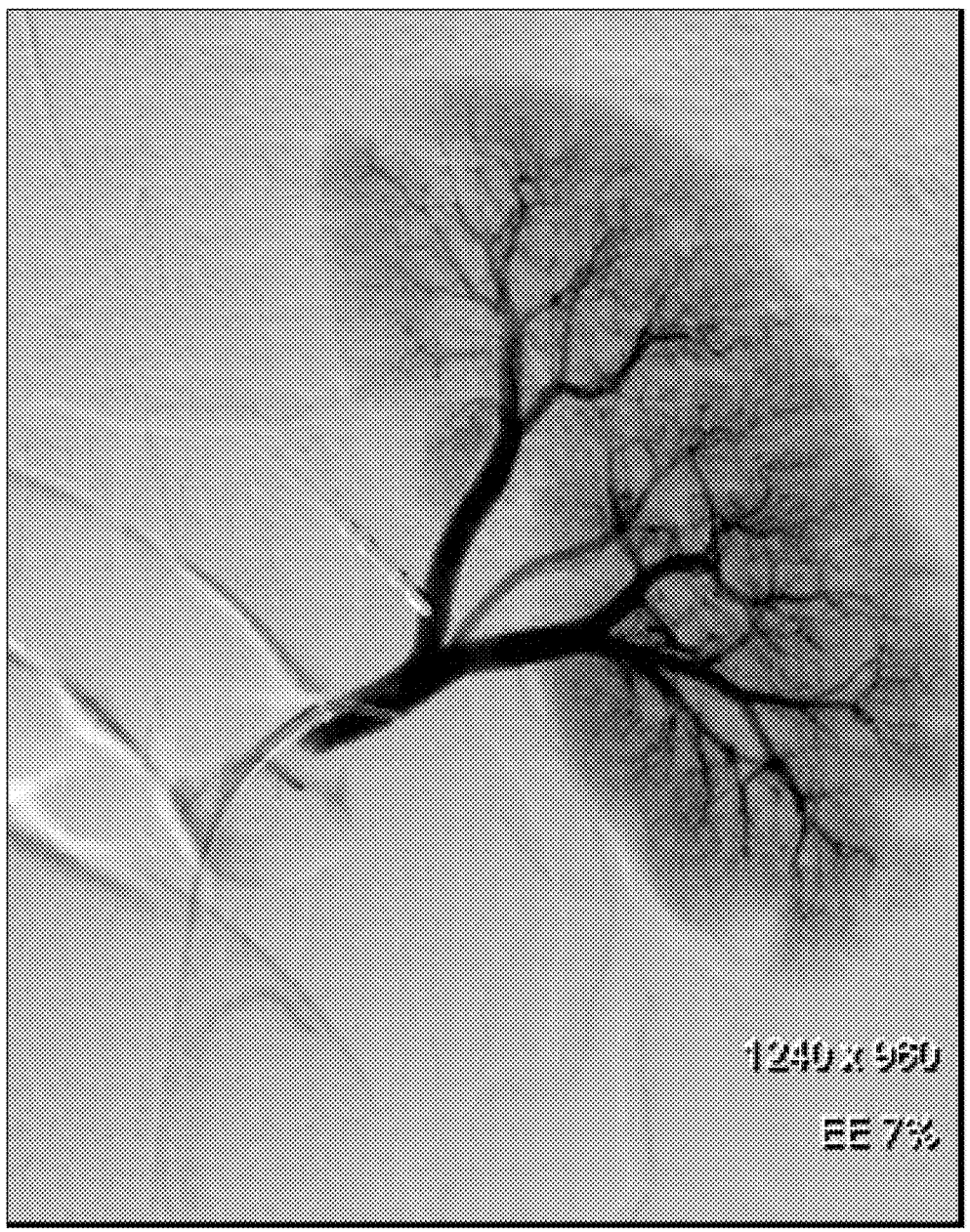
FIG. 19 is a frame capture of a nephrogram performed with stimulation after tissue modification.

After stimulation, catheter was disconnected from stimulator and connected to an electrosurgical generator (Radionics RFG3, Burlington, Mass.). Radiofrequency energy was delivered at an electrode temperature of 70° C. for a period of 90 seconds to ablate the adjacent tissue. Following RF energy delivery, catheter was reconnected to the stimulator and repeat stimulation performed. FIG. 19 is a frame capture of the nephrogram during repeat stimulation showing similar intrarenal vessel emptying and kidney perfusion compared to baseline thus indicating disruption of the renal nerve path. These results demonstrate that a renal physiological response can be detected with percutaneous stimulation and also verification of ganglia or nerve tissue wounding can be determined by reapplying stimulation and analyzing the resulting physiological responses.

There may be other means to modify the aorticorenal ganglia not specifically described in one of the inventions embodiments, but it is to be understood that the description is not meant as a limitation since further modifications may suggest themselves or be apparent to those skilled in the art.

While the present specification has primarily described the detecting and treatment of an aorticorenal ganglion, it should be understood that the same devices and methods can be similarly used to detect and treat any portion of the renal nerves between the aorticorenal ganglion and the kidney.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for treating hypertension comprising:
   advancing a treatment catheter system comprising a plurality of spaced apart tissue stimulation elements and a corresponding plurality of spaced apart tissue modification elements within a patient to a location at or near which an aorticorenal ganglion is thought to exist;
   electrically stimulating said patient with a first of said plurality of spaced apart tissue stimulation elements of said treatment catheter system at said location, without resulting in a permanent change to tissue of the aorticorenal ganglion and/or a permanent change to kidney nerve activity;
   detecting a first physiological response of the patient that indicates said first of said plurality of spaced apart tissue stimulation elements of said treatment catheter system is not in proximity to said aorticorenal ganglion when electrically stimulating said patient with said first of said plurality of spaced apart tissue stimulation elements of said treatment catheter system at said location;

electrically stimulating said patient with a second of said plurality of spaced apart tissue stimulation elements of said treatment catheter system at said location, without resulting in a permanent change to tissue of the aorticorenal ganglion or a permanent change to kidney nerve activity;

detecting a second physiological response of the patient that indicates said second of said plurality of spaced apart tissue stimulation elements of said treatment catheter system is in proximity to said aorticorenal ganglion when electrically stimulating said patient with said second of said plurality of spaced apart tissue stimulation elements of said treatment catheter system at said location;
and ablating said aorticorenal ganglion with a corresponding second of said plurality of spaced apart tissue modification elements of said treatment catheter system when detecting said first physiological response of the patient that indicates said first of said plurality of spaced apart tissue stimulation elements of said treatment catheter system is not in proximity to said aorticorenal ganglion and detecting said second physiological response of the patient that indicates said second of said plurality of spaced apart tissue stimulation elements of said treatment catheter system is in proximity to said aorticorenal ganglion, said ablating resulting in a permanent change to the tissue of the aorticorenal ganglion and/or a permanent change to kidney nerve activity.

2. The method of claim 1, wherein said detecting the second physiological response of the patient that indicates said second of said plurality of spaced apart tissue stimulation elements of said treatment catheter system is in proximity to said aorticorenal ganglion when electrically stimulating said patient with said second of said plurality of spaced apart tissue stimulation elements of said treatment catheter system at said location includes detecting one or more of: a change in renal blood flow velocity, renal vasoconstriction, a change in renal blood flow, and a change in renal artery blood pressure.

3. The method of claim 1, wherein said treatment catheter system comprises one or more catheters that may each perform one or more of said electrically stimulating, detecting, and ablating.

4. The method of claim 1, wherein said treatment catheter system further comprises one or more of: an expandable balloon, an expandable cage, a plurality of arms, or an extendable needle.

5. The method of claim 1 wherein said electric stimulation is between 0.1-100 Hz, 0.1-30 volts, and is pulsed with a pulse duration between 0.1-10 ms.

6. The method of claim 1, wherein said ablating said aorticorenal ganglion further comprises applying radiofrequency energy with said treatment catheter system to said aorticorenal ganglion.

7. The method of claim 1, wherein said detecting the second physiological response of the patient that indicates said second of said plurality of spaced apart tissue stimulation elements of said treatment catheter system is in proximity to said aorticorenal ganglion electrically stimulating said patient with said second of said plurality of spaced apart tissue stimulation elements of said treatment catheter system at said location comprises sensing with one or more sensors selected from the group of: an electromyogram sensor, a thermocouple, a pressure transducer, an ultrasound transducer, and an optical coherence tomography sensor.

8. The method of claim 1, wherein said advancing said treatment catheter system comprising the plurality of spaced apart tissue stimulation elements and the corresponding plurality of spaced apart tissue modification elements within said patient to the location at or near which the aorticorenal ganglion is thought to exist comprises advancing said treatment catheter system within a renal artery, abdominal aorta, vena cava, renal vein, or ostia of said patient.

9. The method of claim 1, wherein said detecting the second physiological response of the patient that indicates said second of said plurality of spaced apart tissue stimulation elements of said treatment catheter system is in proximity to said aorticorenal ganglion when electrically stimulating said patient with said second of said plurality of spaced apart tissue stimulation elements of said treatment catheter system at said location is performed by a control box connected to said catheter treatment system.

10. A method for disrupting kidney nerve signals, comprising:

advancing a treatment catheter comprising a plurality of spaced apart tissue stimulation elements and a corresponding plurality of spaced apart tissue modification elements within a patient to a location of a renal artery near which an aorticorenal ganglion is thought to exist;

electrically stimulating said patient with a first of said plurality of spaced apart tissue stimulation elements of said treatment catheter at said location so as to stimulate an aorticorenal ganglion when said first of said plurality of spaced apart tissue stimulation elements of said treatment catheter is in proximity to said aorticorenal ganglion and without resulting in a permanent change to tissue of the aorticorenal ganglion and/or a permanent change to kidney nerve activity;

detecting a first physiological response of the patient that indicates said first of said plurality of spaced apart tissue stimulation elements of said treatment catheter is not in proximity to said aorticorenal ganglion when electrically stimulating said patient with said first of said plurality of spaced apart tissue stimulation elements of said treatment catheter at said location;

electrically stimulating said patient with a second of said plurality of spaced apart tissue stimulation elements of said treatment catheter at said location so as to stimulate the aorticorenal ganglion when said second of said plurality of spaced apart tissue stimulation elements of said treatment catheter is in proximity to said aorticorenal ganglion and without resulting in a permanent change to the tissue of the aorticorenal ganglion and/or a permanent change to kidney nerve activity;

detecting a second physiological response of the patient that indicates said second of said plurality of spaced apart tissue stimulation elements of said treatment catheter is in proximity to said aorticorenal ganglion when electrically stimulating said patient with said second of said plurality of spaced apart tissue stimulation elements of said treatment catheter at said location;

ablating said aorticorenal ganglion with said treatment catheter so as to disrupt said aorticorenal ganglion in response to detecting the first physiological response of the patient that indicates said first of said plurality of spaced apart tissue stimulation elements of said treatment catheter is not in proximity to said aorticorenal ganglion, and detecting the second physiological response of the patient that indicates said second of said plurality of spaced apart tissue stimulation elements of said treatment catheter is in proximity to said aorticorenal ganglion; and, determining that said kidney nerve signals are permanently disrupted, responsive to said ablating said aorticorenal ganglion.

11. The method of claim 10, wherein said detecting a second physiological response of the patient that indicates said second of said plurality of spaced apart tissue stimulation elements of said treatment catheter is in proximity to said aorticorenal ganglion when electrically stimulating said patient with said second of said plurality of spaced apart tissue stimulation elements of said treatment catheter at said location comprises detecting one or more of the following physiological parameters: a change in renal blood flow, a change in renal blood flow velocity, renal vasoconstriction, and a change in renal artery blood pressure.

12. The method of claim 11, wherein said detecting renal vasoconstriction is performed with one or more of an electromyogram sensor, a thermocouple, a pressure transducer, an ultrasound transducer, and an optical coherence tomography sensor.

13. A treatment system comprising:
a catheter to be positioned in a location in a patient at or near which an aorticorenal ganglion is thought to exist, the catheter comprising:
a plurality of spaced apart electrical stimulation elements;
a sensing element; and,
a plurality of aorticorenal ganglion ablating elements, each co-located with a corresponding one of the plurality of spaced apart electrical stimulation elements; and
a control box in electronic communication with said catheter, said control box to:
activate a first of said plurality of spaced apart electrical stimulation elements in a pattern determined by software executed by said control box when said catheter is positioned in said location in said patient, without resulting in a permanent change to tissue of the aorticorenal ganglion and/or a permanent change to kidney nerve activity;
detect, with said sensing element, a first physiological response of said patient to said activation of said first of said plurality of spaced apart electrical stimulation elements of said catheter at said location in said patient;
determine, based on a communication with said sensing element responsive to said detection of said first physiological response, said first of said plurality of spaced apart electrical stimulation elements of said catheter is not proximate the aorticorenal ganglion when said first of said plurality of spaced apart electrical stimulation elements of said catheter is activated;
activate a second of said plurality of spaced apart electrical stimulation elements in a pattern determined by software executed by said control box when said catheter is positioned in said location in said patient, without resulting in a permanent change to tissue of the aorticorenal ganglion and/or a permanent change to kidney nerve activity;
detect, with said sensing element, a second physiological response of said patient to said activation of said second of said plurality of spaced apart electrical stimulation elements of said catheter at said second location of said patient;
determine, based on a communication with said sensing element responsive to said detection of said second physiological response, said second of said plurality of spaced apart electrical stimulation elements of said catheter is proximate the aorticorenal ganglion when said second of said plurality of spaced apart electrical stimulation elements of said catheter is activated; and
activate a second of said plurality of aorticorenal ganglion ablating elements corresponding to said second of said plurality of spaced apart electrical stimulation elements, said second of said plurality of aorticorenal ganglion ablating elements to permanently change tissue of said aorticorenal ganglion in response to said determination that said first of said plurality of spaced apart electrical stimulation elements of said catheter is not proximate the aorticorenal ganglion when said first of said plurality of spaced apart electrical stimulation elements of said catheter is activated and further in response to said determination that said second of said plurality of spaced apart electrical stimulation elements of said catheter is proximate to said aorticorenal ganglion, resulting in a permanent change to tissue of the aorticorenal ganglion and/or a permanent change of kidney nerve activity.

14. The treatment system of claim 13, wherein said catheter comprises an element selected from a group consisting of: an expandable balloon, a helical member, an expandable cage, a plurality of arms, and an extendable needle.

15. The treatment system of claim 13, wherein said control box to communicate with said sensing element to detect said first or second physiological response includes said sensing element to detect one or more of: a change in renal blood flow, a change in renal blood flow velocity, renal vasoconstriction, and a change in renal artery blood pressure.

16. The treatment system of claim 13, wherein each of said plurality of aorticorenal ganglion ablating elements is configured to direct aorticorenal ganglion modifying energy in a radial direction towards said aorticorenal ganglion.

17. The treatment system of claim 13, wherein each of said plurality of aorticorenal ganglion ablating elements is configured to direct aorticorenal ganglion modifying energy in an axial direction towards said aorticorenal ganglion.

18. A method for treating hypertension comprising:
advancing a treatment catheter system comprising a plurality of spaced apart tissue stimulation elements and a corresponding plurality of co-located tissue modification elements within a patient to or near a location at which an aorticorenal ganglion is thought to exist;
electrically stimulating said patient with a first of said plurality of spaced apart tissue stimulation elements of said treatment catheter system at said location, without resulting in a permanent change to tissue of the aorticorenal ganglion and/or a permanent change to kidney nerve activity;
detecting a first physiological response of the patient that indicates said first of said plurality of spaced apart tissue stimulation elements of said treatment catheter system is not in proximity to the aorticorenal ganglion when electrically stimulating said patient with said first of said plurality of spaced apart tissue stimulation elements of said treatment catheter system at said location;

electrically stimulating said patient with a second of said plurality of spaced apart tissue stimulation elements of said treatment catheter system at said location, without resulting in a permanent change to tissue of the aorticorenal ganglion and/or a permanent change to kidney nerve activity;

detecting a second physiological response of the patient that indicates said second of said plurality of spaced apart tissue stimulation elements of said treatment catheter system is in proximity to the aorticorenal ganglion when electrically stimulating said patient with said second of said plurality of spaced apart tissue stimulation elements of said treatment catheter system at said location; and directing aorticorenal ganglion modifying energy towards said aorticorenal ganglion with a second of said plurality of aorticorenal ganglion ablating elements that is co-located with said second of said plurality of spaced apart electrical stimulation elements while said location of said second of said plurality of tissue stimulation elements of said treatment catheter system is in proximity to said aorticorenal ganglion at said location, in response to detecting the first physiological response of the patient that indicates said first of said plurality of stimulation elements of said treatment catheter system is not in proximity to the aorticorenal ganglion when electrically stimulating said patient with said first of said plurality of stimulation elements of said treatment catheter system at said location, and in response to the detecting the second physiological response of the patient that indicates said second of said plurality of stimulation elements of said treatment catheter system is in proximity to the aorticorenal ganglion when electrically stimulating said patient with said second of said plurality of stimulation elements of said treatment catheter system at said location, resulting in the permanent change to tissue of the aorticorenal ganglion and/or the permanent change to kidney nerve activity.

19. The method of claim 18, wherein directing aorticorenal ganglion modifying energy towards said aorticorenal ganglion is performed axially or radially, or a combination thereof.

20. The method of claim 18, wherein said directing aorticorenal ganglion modifying energy towards said aorticorenal ganglion creates permanent tissue modification in said proximity of said aorticorenal ganglion in a shape of a half toroid.

21. The method of claim 2, wherein said detecting is performed with one or more of an electromyogram sensor, a thermocouple, a pressure transducer, an ultrasound transducer, and an optical coherence tomography sensor.

22. A method of ablating an aorticorenal ganglion in a human, wherein the aorticorenal ganglion is coupled to but separate from a renal plexus, the method comprising:

inserting an apparatus into a location in a body lumen of the human near which the aorticorenal ganglion is thought to exist, the apparatus comprising a plurality of electrical stimulation elements, a corresponding plurality of aorticorenal ganglion ablation elements, and an aorticorenal ganglion detection element;

activating a first of the plurality of the electrical stimulation elements after the apparatus is inserted into the location in the body lumen, the activated first of the plurality of electrical stimulation elements to stimulate the aorticorenal ganglion when the aorticorenal ganglion is near the first of the plurality of electrical stimulation elements, without resulting in a permanent change to tissue of the aorticorenal ganglion and/or a permanent change to kidney nerve activity;

activating the aorticorenal ganglion detection element to detect a first physiological change in the human in response to activation of the first of the plurality of electrical stimulation elements, the first physiological change indicating the aorticorenal ganglion is not near the first of the plurality of electrical stimulation elements;

activating a second of the plurality of electrical stimulation elements after the apparatus is inserted into the location in the body lumen, the activated second of the plurality of electrical stimulation elements to stimulate the aorticorenal ganglion when the aorticorenal ganglion is near the second of the plurality of electrical stimulation elements, without resulting in a permanent change to tissue of the aorticorenal ganglion and/or a permanent change to kidney nerve activity;

activating the aorticorenal ganglion detection element to detect a second physiological change in the human in response to activation of the second of the plurality of electrical stimulation elements, the second physiological change indicating the aorticorenal ganglion is near the second of the plurality of electrical stimulation elements; and activating a corresponding second of the plurality of aorticorenal ganglion ablation elements while the apparatus remains at the location in the body lumen to ablate the aorticorenal ganglion, responsive to the aorticorenal ganglion detection element detecting the first physiological change and the second physiological change in the human, resulting in the permanent change to tissue of the aorticorenal ganglion and/or a permanent change to kidney nerve activity.

23. The method of claim 22, wherein activating the corresponding second of the plurality of co-located aorticorenal ganglion ablation elements while the apparatus remains at the location in the body lumen to ablate the aorticorenal ganglion comprises activating the corresponding second of the plurality of co-located aorticorenal ganglion ablation elements while the apparatus remains at the location in the body lumen to ablate the aorticorenal ganglion to cause disruption to kidney nerve activity.

24. The method of claim 22, wherein the body lumen is selected from a group of body lumens consisting of: a renal artery, an abdominal aorta, a vena cava, a renal vein, and ostia thereof.

25. The method of claim 22, wherein the apparatus comprising the plurality of electrical stimulation elements, the corresponding plurality of co-located aorticorenal ganglion ablation elements, and the aorticorenal ganglion detection element, and combinations thereof, are arranged into one of a one-, two-, or three-catheter assembly.

26. The method of claim 22, wherein each of the plurality of electrical stimulation elements and a corresponding one of the plurality of aorticorenal ganglion ablation elements are the same element.

27. The method of claim 22, wherein activating the aorticorenal ganglion detection element to detect the second physiological change in the human in response to activation of the second of the plurality of electrical stimulation elements, wherein the second physiological change indicates the aorticorenal ganglion is near the second of the plurality of electrical stimulation elements, comprises detecting one or more physiological changes consisting of: renal vasoconstriction, decreased renal blood flow, reduced glomerular filtration rate, pulsation of a kidney, and pulsation of renal vasculature.

28. An apparatus to permanently modify tissue of an aorticorenal ganglion in a human, wherein the aorticorenal ganglion is coupled to but separate from a renal plexus, the apparatus comprising:
- a catheter system to insert into a location in a body lumen of the human, near which the aorticorenal ganglion is thought to exist, the catheter system comprising:
    - a plurality of electrical stimulation elements;
    - a physiological measurement element; and
    - a plurality of aorticorenal ganglion modification elements, each co-located with a corresponding one of the plurality of electrical stimulation elements;
- a control box in electronic communication with said catheter system, said control box to:
    - activate a first of the plurality of electrical stimulation elements when the catheter system is inserted into the location in the body lumen, the activated first of the plurality of electrical stimulation elements to stimulate the aorticorenal ganglion when the aorticorenal ganglion is near the first of the plurality of electrical stimulation elements, without resulting in a permanent modification of tissue of the aorticorenal ganglion and/or a permanent decrease of kidney nerve activity;
    - measure with the physiological measurement element a first physiological response in the human in response to activation of the first of the plurality of electrical stimulation elements, the first physiological response indicating the aorticorenal ganglion is not near the first of the plurality of electrical stimulation elements;
    - activate a second of the plurality of electrical stimulation elements when the catheter system is inserted into the location in the body lumen, the activated second of the plurality of electrical stimulation elements to stimulate the aorticorenal ganglion when the aorticorenal ganglion is near the second of the plurality of electrical stimulation elements, without resulting in a permanent modification of tissue of the aorticorenal ganglion and/or a permanent decrease of kidney nerve activity;
    - measure with the physiological measurement element a second physiological response in the human in response to activation of the second of the plurality of electrical stimulation elements, the second physiological response indicating the aorticorenal ganglion is near the second of the plurality of electrical stimulation elements;
    - activate a second of the plurality of aorticorenal ganglion modification elements co-located with the second of the plurality of electrical stimulation elements, while the catheter system remains inserted into the location in the body lumen, to modify the aorticorenal ganglion in response to the physiological measurement element measuring the second physiological response in the human, resulting in the permanent modification of tissue of the aorticorenal ganglion and/or the permanent decrease of kidney nerve activity.

29. The apparatus of claim 28, wherein the catheter system comprises one of a one-, two-, or three-catheter assembly.

30. The apparatus of claim 28, wherein each of the plurality of electrical stimulation elements and each of the plurality of aorticorenal ganglion modification elements that is co-located with a corresponding electrical stimulation element are the same element.

31. The apparatus of claim 28, wherein the control box to measure with the physiological measurement element the first or the second physiological response in the human comprises the control box to measure with the physiological measurement element one or more physiological responses consisting of: renal vasoconstriction, decreased renal blood flow, reduced glomerular filtration rate, pulsation of a kidney, and pulsation of renal vasculature.

* * * * *